(12) United States Patent  (10) Patent No.: US 8,008,414 B2
Yamago et al.  (45) Date of Patent: Aug. 30, 2011

(54) ORGANIC ANTIMONY COMPOUND, PROCESS FOR PRODUCING THE SAME, LIVING RADICAL POLYMERIZATION INITIATOR, PROCESS FOR PRODUCING POLYMER USING THE SAME, AND POLYMER

(75) Inventors: Shigeru Yamago, Osaka (JP); Biswajit Ray, West Bengal (IN); Takashi Kameshima, Tokushima (JP); Kazuhiro Kawano, Tokushima (JP)

(73) Assignees: Otsuka Chemical Co., Ltd., Osaka (JP); Japan Science and Technology Agency, Saitama (JP)

( * ) Notice: Subject to any disclaimer, the term of this patent is extended or adjusted under 35 U.S.C. 154(b) by 612 days.

(21) Appl. No.: 11/630,667

(22) PCT Filed: Jun. 23, 2005

(86) PCT No.: PCT/JP2005/012016
§ 371 (c)(1),
(2), (4) Date: Jun. 24, 2009

(87) PCT Pub. No.: WO2006/001496
PCT Pub. Date: Jan. 5, 2006

(65) Prior Publication Data
US 2009/0299008 A1    Dec. 3, 2009

(30) Foreign Application Priority Data

Jun. 23, 2004  (JP) ................................ 2004-185493
Sep. 13, 2004  (JP) ................................ 2004-265223

(51) Int. Cl.
*B01J 23/18* (2006.01)
*C07F 9/90* (2006.01)
*C07F 9/92* (2006.01)
*C08F 4/72* (2006.01)

(52) U.S. Cl. ............... 526/218.1; 502/150; 502/152; 502/155; 502/171; 502/353; 526/183; 526/190; 526/192; 526/219; 526/219.1; 526/219.2; 526/219.3; 556/64; 556/70

(58) Field of Classification Search .................. 502/150, 502/152, 155, 171, 353; 526/183, 190, 192, 526/218.1, 219, 219.1, 219.2, 219.3; 556/64, 556/70
See application file for complete search history.

(56) References Cited

U.S. PATENT DOCUMENTS

| 2,833,741 | A | * | 5/1958 | Lal | ............... | 525/248 |
| 7,276,569 | B2 | | 10/2007 | Yamago et al. | | |
| 2005/0245714 | A1 | | 11/2005 | Yamago et al. | | |
| 2008/0004366 | A1 | * | 1/2008 | Yamago et al. | ............... | 522/49 |

FOREIGN PATENT DOCUMENTS

| EP | 1 541 550 A1 | 6/2005 |
| FR | 1587586 | 3/1970 |
| GB | 1 286 755 A | 8/1972 |
| JP | 2003005372 | 1/2003 |
| WO | 2004/014848 A1 | 2/2004 |

OTHER PUBLICATIONS

Yamago et al., "Highly versatile organostibine mediators for living radical polymerization", J Am Chem Soc 2004, 126, 13908-13909.*
Foss et al., "Electronic factors and the structure of organoantimony carbonyl compounds.", J Organomet Chem 1974, 78(1), 115-126.*
Foss, V.L. et al., "Electronic Factors and the Structure of Organoantimony Carbonyl Compounds. Organoantimony Derivatives of Aliphatic-Aromatic Ketones", J. Organomet. Chem. 1974, 78(1), 115-126.*
Yamago, S. et al., "Highly Versatile Organostibine Mediators for Living Radical Polymerization", J. Am. Chem. Soc. 2004, 126(43), 13908-13909.*
Yamago, S., "Novel Group-Transfer Radical Reactions with Organotelluriums", Synlett 2004, 11, 1875-1890.*
Supplementary European Search Report issued Mar. 3, 2008 in the European Application No. EP 05 75 5674.
Foss, V.L. et al., "Spatial Effects and the Structure of Organoantimony Aldehydes and Ketones," Journal of Organometallic Chemistry, vol. 78, No. 1, 1974, pp. 107-113, XP002467630.
Burg, A.B. et al., "The Methylstibines and the Monomer Dimethylstibinoborine", Journal of the American Chemical Society, vol. 81, No. 1, 1959, pp. 1-5, XP002467631.
Burg, A.B., "Restudy of Dimethylstibinoborine", Inorganic Chemistry, vol. 16, No. 1, 1977, pp. 217-218, XP002467632.
Amberger, E. et al., "Mixed Organometallic Compounds of Group V I. Synthesis of Tris(Trimethyl-Group-IV)Stibines", Journal of Organometallic Chemistry, vol. 8, No. 1, 1967, pp. 111-114, XP002467633.
Barton, D.H.R. et al., "The Invention of Radical Reactions. Part XVIII. Decarboxylative Radical Addition to Arsenic, Antimony, and Bismuth Phenylsulphides—A Novel Synthesis of Nor-Alcohols from Carboxylic Acids", Tetrahedron, vol. 45, No. 9, 1989, pp. 2615-2626, XP002467635.
Barrett, A.G.M., et al., "Tetraphenyl Distibine: A Most Useful Reagent for Discriminating Radical Reactions", J. Am. Chem. Soc., 1991, vol. 113, No. 21, 1991, pp. 8177-8178, XP002467634.

(Continued)

*Primary Examiner* — Vasu Jagannathan
*Assistant Examiner* — Richard A Huhn
(74) *Attorney, Agent, or Firm* — Wenderoth, Lind & Ponack, L.L.P.

(57) ABSTRACT

An organoantimony compound represented by the formula (1), processes for producing polymers with use of the compound, and polymers

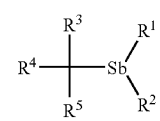

(1)

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, oxycarbonyl or cyano.

25 Claims, No Drawings

OTHER PUBLICATIONS

Davies, A.G. et al., "Homolytic Organometallic Reactions. Part III. An Electron Spin Resonance Study of Homolytic t-Butoxydealkylation of Organometallic Compounds. Rate Constants for the Reaction at Boron", Journal of Chemical Society B., 1971, pp. 1823-1829, XP009095588.

Ando Fumio, et al., Insertion of Ketene and Diphenylketene to the Pnictogen-Heteroatom Bonds, Bull. Chem. Soc. Jpn., 1987, vol. 60, pp. 1564 to 1566.

* cited by examiner

ORGANIC ANTIMONY COMPOUND, PROCESS FOR PRODUCING THE SAME, LIVING RADICAL POLYMERIZATION INITIATOR, PROCESS FOR PRODUCING POLYMER USING THE SAME, AND POLYMER

TECHNICAL FIELD

The present invention relates to organoantimony compounds and a process for preparing the same. More particularly, the invention relates to living radical polymerization initiators of the organoantimony type, a process for preparing living radical polymers using the initiator and living radical polymers. The present invention also relates to a process for preparing a random copolymer and the random copolymer, a process for preparing a block copolymer and the block copolymer, and these macro living radical polymerization initiators and polymers.

Further, the polymer of the present invention is suitable for use as a resist material and the like usable for preparing a semiconductor device.

BACKGROUND ART

Living radical polymerization is a polymerization process which is adapted for precision control of molecular structures while ensuring convenience and universal usefulness of radical polymerization, and is powerful means for preparing novel high polymer materials. The present inventors have reported, as an example, a living radical polymerization using an organotellurium compound as an initiator (for example, patent literature 1).

[patent literature 1] WO 2004/14848

The process of patent literature 1 makes it possible to control molecular weights and molecular weight distributions, but utilizes an organotellurium initiator and has no disclosure about organoantimony compounds of the present invention.

An object of the present invention is to provide a process for preparing living radical polymers and the polymers, which makes possible precision control of molecular weights and molecular weight distributions (PD=Mw/Mn), by polymerizing a vinyl monomer using an organoantimony compound.

An object of the present invention is to provide a process for preparing living radical polymers and the polymers, which makes possible precision control of molecular weights and molecular weight distributions (PD=Mw/Mn) under mild conditions, in short period of time and in high yield for preparing the compound, a process for producing a polymer with use of the compound, and the polymer.

DISCLOSURE OF THE INVENTION

1. An organoantimony compound represented by the formula (1)

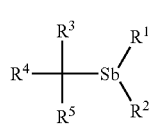

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, oxycarbonyl or cyano.

2. A process for preparing an organoantimony compound of the formula (1) comprising reacting a compound of the formula (3), and a compound of the formula (4) or (5)

(wherein $R^1$ and $R^2$ are as defined above, and Z is a halogen atom or alkali metal)

(wherein $R^3$, $R^4$ and $R^5$ are as defined above, and X is a halogen atom)

(wherein $R^3$, $R^4$ and $R^5$ are as defined above)

3. A living radical polymerization initiator of the formula (2)

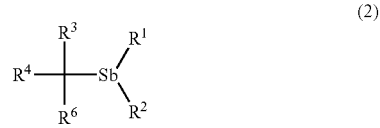

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^6$ is aryl, substituted aryl, an aromatic heterocyclic group, acyl, oxycarbonyl or cyano.

4. A process for producing a living radical polymer characterized in that a vinyl monomer is polymerized with use of a living radical polymerization initiator of the formula (2).

5. A process for producing a living radical polymer characterized in that a vinyl monomer is polymerized with use of a living radical polymerization initiator of the formula (2) and an azo type polymerization initiator.

6. A process for producing a random copolymer characterized in that at least two vinyl monomers are polymerized with use of a living radical polymerization initiator of the formula (2), or this initiator and an azo type polymerization initiator.

7. A macro living radical polymerization initiator which is obtainable by subjecting a vinyl monomer to polymerization with use of a living radical polymerization initiator of the formula (2), or this initiator and an azo type polymerization initiator.

8. A process for producing a living radical polymer characterized in that a vinyl monomer is polymerized with use of a living radical polymerization initiator of the formula (2), at least one compound selected from ditelluride compound, distibine compound and dibismuthine compound, and as required an azo type polymerization initiator.

9. A process for producing a resin containing an acid-dissociable group characterized in that a vinyl monomer is polymerized with use of one of the following (a) to (d),
(a) a living radical polymerization initiator of the formula (2),
(b) a mixture of a living radical polymerization initiator of the formula (2), and an azo type polymerization initiator,
(c) a mixture of a living radical polymerization initiator of the formula (2), and at least one compound selected from ditelluride compound, distibine compound and dibismuthine compound, and
(d) a mixture of a living radical polymerization initiator of the formula (2), an azo type polymerization initiator, and at least one compound selected from ditelluride compound, distibine compound and dibismuthine compound.

10. A radiation-sensitive resin composition comprising a resin containing an acid-dissociable group, and a radiation-sensitive acid producing agent.

The organoantimony compounds of the present invention are represented by the formula (1)

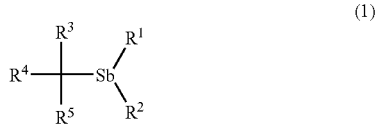

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, oxycarbonyl or cyano.

Examples of groups represented by $R^1$ and $R^2$ are as follows.

Examples of $C_1$-$C_8$ alkyl groups usable are straight-chain, branched chain or cyclic alkyl groups having 1 to 8 carbon atoms, such as methyl, ethyl, n-propyl, isopropyl, cyclopropyl, n-butyl, sec-butyl, tert-butyl, cyclobutyl, n-pentyl, n-hexyl, n-heptyl and n-octyl. Preferable alkyl groups are straight-chain or branched chain alkyl groups having 1 to 4 carbon atoms. Methyl, ethyl or n-butyl is more preferable.

Examples of aryl groups are phenyl and naphthyl. Preferable is phenyl. Examples of substituted aryl groups are phenyl having a substituent and naphthyl having a substituent.

Examples of substituents of aryl groups having a substituent are a halogen atom, hydroxyl, alkoxyl, amino, nitro, cyano, carbonyl-containing groups represented by —$COR^a$ ($R^a$=$C_1$-$C_8$ alkyl, aryl, $C_1$-$C_8$ alkoxyl or aryloxy), sulfonyl, trifluoromethyl, etc. Preferable aryl group having a substituent is trifluoromethyl-substituted phenyl. Preferably such substituted groups have one or two substituents at the para-position or ortho-position. Examples of aromatic heterocyclic groups are pyridyl, pyrrol, furyl and thienyl.

Examples of groups represented by $R^3$ and $R^4$ are as follows.

Examples of $C_1$-$C_8$ alkyl groups usable are the same as the alkyl groups represented by $R^1$ and given above.

Examples of groups represented by $R^5$ are as follows.

Examples of aryl, substituted aryl, aromatic heterocyclic groups usable are the same as those groups represented by $R^1$ and given above.

Examples of preferred oxycarbonyl groups are those represented by —$COOR^b$ ($R^b$=H, $C_1$-$C_8$ alkyl or aryl) such as carboxyl, methoxycarbonyl, ethoxycarbonyl, propoxycarbonyl, n-butoxycarbonyl, sec-butoxycarbonyl, ter-butoxycarbonyl, n-pentoxycarbonyl and phenoxycarbonyl. Methoxycarbonyl and ethoxycarbonyl are more desirable oxycarbonyl groups.

Examples of preferred groups represented by $R^5$ are aryl, substituted aryl, oxycarbonyl and cyano. The aryl group is preferably phenyl. Examples of preferred substituted aryl groups are phenyl substituted with a halogen atom and phenyl substituted with trifluoromethyl. When the substituent is a halogen, the phenyl is substituted with preferably one to five halogen atoms. In the case of alkoxyl or trifluoromethyl, preferably one or two substituents are present. When having one substituent, the group is substituted preferably at the para- or ortho-position. When the group has two substituents, the meta-positions are preferred. Examples of preferred oxycarbonyl groups are methoxycarbonyl and ethoxycarbonyl.

Examples of preferred organoantimony compounds represented by the formula (1) are compounds wherein $R^1$ and $R^2$ are $C_4$ alkyl, $R^3$ and $R^4$ are each a hydrogen atom or $C_1$-$C_4$ alkyl, and $R^5$ is aryl, substituted aryl or oxycarbonyl. Especially preferable organotellurium compounds are those wherein $R^1$ and $R^2$ are $C_1$-$C_4$ alkyl, $R^3$ and $R^4$ are each a hydrogen atom or $C_1$-$C_4$ alkyl, and $R^5$ is phenyl, substituted phenyl, methoxycarbonyl or ethoxycarbonyl.

Examples of organoantimony compounds represented by the formula (1) are as follows.

(Dimethylstibanyl-methyl)benzene, (1-dimethylstibanyl-ethyl)benzene, (2-dimethylstibanyl-propyl)benzene, 1-chloro-4-(dimethylstibanyl-methyl)benzene, 1-hydroxy-4-(dimethylstibanyl-methyl)benzene, 1-methoxy-4-(dimethylstibanyl-methyl)benzene, 1-amino-4-(dimethylstibanyl-methyl)benzene, 1-nitro-4-(dimethylstibanyl-methyl)benzene, 1-cyano-4-(dimethylstibanyl-methyl)benzene, 1-methylcarbonyl-4-(dimethylstibanyl-methyl)benzene, 1-phenylcarbonyl-4-(dimethylstibanyl-methyl)benzene, 1-methoxycarbonyl-4-(dimethylstibanyl-methyl)benzene, 1-phenoxycarbonyl-4-(dimethylstibanyl-methyl)benzene, 1-sulfonyl-4-(dimethylstibanyl-methyl)benzene, 1-trifluoromethyl-4-(dimethylstibanyl-methyl)benzene, 1-chloro-4-(1-dimethylstibanyl-ethyl)benzene, 1-hydroxy-4-(1-dimethylstibanyl-ethyl)benzene, 1-methoxy-4-(1-dimethylstibanyl-ethyl)benzene, 1-amino-4-(1-dimethylstibanyl-ethyl)benzene, 1-nitro-4-(1-dimethylstibanyl-ethyl)benzene, 1-cyano-4-(1-dimethylstibanyl-ethyl)benzene, 1-methylcarbonyl-4-(1-dimethylstibanyl-ethyl)benzene, 1-phenylcarbonyl-4-(1-dimethylstibanyl-ethyl)benzene, 1-methoxycarbonyl-4-(1-dimethylstibanyl-ethyl)benzene, 1-phenoxycarbonyl-4-(1-dimethylstibanyl-ethyl)benzene, 1-sulfonyl-4-(1-dimethylstibanyl-ethyl)benzene, 1-trifluoromethyl-4-(1-dimethylstibanyl-ethyl)benzene, 1-(1-dimethylstibanyl-ethyl)-3,5-bis-trifluoromethylbenzene, 1,2,3,4,5-pentafluoro-6-(1-dimethylstibanyl-ethyl)benzene, 1-chloro-4-(2-dimethylstibanyl-propyl)benzene, 1-hydroxy-4-(2-dimethylstibanyl-propyl)benzene, 1-methoxy-4-(2-dimethylstibanyl-propyl)benzene, 1-amino-4-(2-dimethylstibanyl-propyl)benzene, 1-nitro-4-(2-dimethylstibanyl-propyl)benzene, 1-cyano-4-(2-dimethylstibanyl-propyl)benzene, 1-methylcarbonyl-4-(2-dimethylstibanyl-propyl)benzene, 1-phenylcarbonyl-4-(2-dimethylstibanyl-propyl)benzene, 1-methoxycarbonyl-4-(2-dimethylstibanyl-propyl)benzene, 1-phenoxycarbonyl-4-(2-dimethylstibanyl-propyl)benzene, 1-sulfonyl-4-(2-dimethylstibanyl-propyl)benzene, 1-trifluoromethyl-4-(2-dimethylstibanyl-propyl)benzene, 2-(dimethylstibanyl-methyl)pyridine, 2-(1-dimethylstibanyl-ethyl)pyridine, 2-(2-dimethylstibanyl-propyl)pyridine, methyl 2-dimethylstibanyl-acetate, methyl 2-dimethylstibanyl-propionate, methyl 2-dimethylstibanyl-2-methylpropionate, ethyl 2-dimethylstibanyl-acetate, ethyl 2-dimethylstibanyl propionate, ethyl 2-dimethylstibanyl-2-methylpropionate [ethyl-2-methyl-2-dimethylstibanyl-propionate], ethyl 2-(di-n-butylstibanyl)-2-methylpropionate [ethyl-2-methyl-2-di-n-butylstibanyl-propionate], 2-dimethylstibanyl-acetonitrile, 2-dimethylstibanyl-propionitrile, 2-methyl-2-dimethylstibanyl-propionitrile, (diphenylstibanyl-methyl)benzene, (1-diphenylstibanyl-ethyl)benzene, (2-diphenylstibanyl-propyl)benzene, etc. The above compounds also include all compounds having diethylstibanyl, 1-diethylstibanyl, 2-diethylstibanyl, di-n-butylstibanyl, 1-di-n-butylstibanyl, 2-di-n-butylstibanyl, diphenylstibanyl, 1-diphenylstibanyl or 2-diphenylstibanyl, as changed from the portion of dimethylstibanyl, 1-dimethylstibanyl or 2-dimethylstibanyl.

Preferable are (dimethylstibanyl-methyl)benzene, (1-dimethylstibanyl-ethyl)benzene, (2-dimethylstibanyl-propyl)benzene, 1-chloro-4-(dimethylstibanyl-methyl)benzene, 1-trifluoromethyl-4-(1-dimethylstibanyl-ethyl)benzene, methyl 2-dimethylstibanyl-2-methylpropionate, ethyl 2-dimethylstibanyl-2-methylpropionate[ethyl-2-methyl-2-dimethylstibanyl-propionate], ethyl 2-(di-n-butylstibanyl)-2-methylpropionate[ethyl-2-methyl-2-di-n-butylstibanyl-propionate], 1-(1-dimethylstibanyl-ethyl)-3,5-bis-trifluoromethylbenzene, 1,2,3,4,5-pentafluoro-6-(1-dimethylstibanyl-ethyl)benzene, 2-dimethylstibanyl-propionitrile, 2-methyl-2-dimethylstibanyl-propionitrile, (diethylstibanyl-methyl)benzene, (1-diethylstibanyl-ethyl)benzene, (2-diethylstibanyl-propyl)benzene, methyl 2-diethylstibanyl-2-methylpropionate, ethyl 2-diethylstibanyl-2-methylpropionate, 2-diethylstibanyl-propionitrile, 2-methyl-2-diethylstibanyl-propionitrile, (di-n-butylstibanyl-methyl)benzene, (1-di-n-butylstibanyl-ethyl)benzene, (2-di-n-butylstibanyl-propyl)benzene, methyl 2-di-n-butylstibanyl-2-methylpropionate, ethyl 2-di-n-butylstibanyl-2-methylpropionate, 2-di-n-butylstibanyl propionitrile, 2-methyl-2-di-n-butylstibanyl propionitrile.

The organoantimony compound represented by the formula (1) can be prepared by reacting a compound of the formula (3) and, a compound of the formula (4) or a compound of the formula (5)

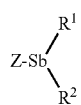

(3)

(wherein $R^1$ and $R^2$ are defined above, and Z is a halogen atom or alkali metal)

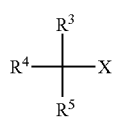

(4)

(wherein $R^3$, $R^4$ and $R^5$ are defined above, and X is a halogen atom)

(5)

(wherein $R^3$, $R^4$ and $R^5$ are defined above)

Examples of compounds represented by the formula (3) are as follows

Examples of groups represented by $R^1$ and $R^2$ are as given above.

Examples of groups represented by Z are halogen atom such as fluorine, chlorine, bromine or iodine or alkali metal such as sodium, potassium or lithium. Preferable are chlorine, bromine, sodium and lithium.

Examples of compound (3) are dimethylstibanyl bromide, diethylstibanyl bromide, di-n-butylstibanyl bromide, diphenylstibanyl bromide, dimethylstibanyl sodium, diethylstibanyl sodium, di-n-butylstibanyl sodium and diphenylstibanyl sodium. The above compounds also include all compounds having chloride or iodide, as changed from the portion of bromide. Further, the above compounds also include all compounds having potassium or lithium, as changed from the portion of sodium.

Examples of compounds represented by the formula (4) are as follows

Examples of groups represented by $R^3$, $R^4$ and $R^5$ are as given above.

Examples of groups represented by X can be a halogen atom such as fluorine, chlorine, bromine or iodine. Chlorine and bromine are preferable.

Examples of compounds usable are benzyl chloride, benzyl bromide, 1-chloro-1-phenylethane, 1-bromo-1-phenylethane, 2-chloro-2-phenylpropane, 2-bromo-2-phenylpropane, p-chlorobenzyl chloride, p-hydroxybenzyl chloride, p-methoxybenzyl chloride, p-aminobenzyl chloride, p-nitrobenzyl chloride, p-cyanobenzyl chloride, p-methylcarbonylbenzyl chloride, phenylcarbonylbenzyl chloride, p-methoxycarbonylbenzyl chloride, p-phenoxycarbonylbenzyl chloride, p-sulfonylbenzyl chloride, p-trifluoromethylbenzyl chloride, 1-chloro-1-(p-chlorophenyl)ethane, 1-bromo-1-(p-chlorophenyl)ethane, 1-chloro-1-(p-hydroxyphenyl)ethane, 1-bromo-1-(p-hydroxyphenyl)-ethane, 1-chloro-1-(p-methoxyphenyl)ethane, 1-bromo-1-(p-methoxyphenyl)ethane, 1-chloro-1-(p-aminophenyl)ethane, 1-bromo-1-(p-aminophenyl)ethane, 1-chloro-1-(p-nitrophenyl)ethane, 1-bromo-1-(p-nitrophenyl)ethane, 1-chloro-1-(p-cyanophenyl)ethane, 1-bromo-1-(p-cyanophenyl)ethane, 1-chloro-1-(p-methylcarbonylphenyl)ethane, 1-bromo-1-(p-methylcarbonylphenyl)ethane, 1-chloro-1-(p-phenylcarbonylphenyl)ethane, 1-bromo-1-(p-phenylcarbonylphenyl)-ethane, 1-chloro-1-(p-methoxycarbonylphenyl)ethane, 1-bromo-1-(p-methoxycarbonylphenyl)ethane, 1-chloro-1-(p-phenoxycarbonylphenyl)-ethane, 1-bromo-1-(p-phenoxycarbonylphenyl)ethane, 1-chloro-1-(p-sulfonylphenyl)ethane, 1-bromo-1-(p-sulfonylphenyl)ethane, 1-chloro-1-(p-trifluoromethylphenyl)ethane, 1-bromo-1-(p-trifluoromethylphenyl)ethane, 2-chloro-2-(p-chlorophenyl)propane, 2-bromo-2-(p-chlorophenyl)propane, 2-chloro-2-(p-hydroxyphenyl)-propane, 2-bromo-2-(p-hydroxyphenyl)propane, 2-chloro-2-(p-methoxyphenyl)propane, 2-bromo-2-(p-methoxyphenyl)propane, 2-chloro-2-(p-aminophenyl)propane, 2-bromo-2-(p-aminophenyl)propane, 2-chloro-2-(p-nitrophenyl)propane, 2-bromo-2-(p-nitrophenyl)-propane, 2-chloro-2-(p-cyanophenyl)propane, 2-bromo-2-(p-cyanophenyl)propane, 2-chloro-2-(p-methylcarbonylphenyl)propane, 2-bromo-2-(p-methylcarbonylphenyl)propane, 2-chloro-2-(p-phenylcarbonylphenyl)propane, 2-bromo-2-(p-phenylcarbonylphenyl)-propane, 2-chloro-2-(p-methoxycarbonylphenyl)propane, 2-bromo-2-(p-methoxycarbonylphenyl)propane, 2-chloro-1-(p-phenoxycarbonylphenyl)propane, 2-bromo-2-(p-phenoxycarbonylphenyl)propane, 2-chloro-2-(p-sulfonylphenyl)propane, 2-bromo-2-(p-sulfonylphenyl)propane, 2-chloro-2-(p-trifluoromethylphenyl)propane, 2-bromo-2-(p-trifluoromethylphenyl)propane, 2-(chloromethyl)pyridine, 2-(bromomethyl)pyridine, 2-(1-chloroethyl)pyridine, 2-(1-bromoethyl)pyridine, 2-(2-chloropropyl)pyridine, 2-(2-bromopropyl)pyridine, methyl 2-chloroacetate, methyl 2-bromoacetate, methyl 2-chloropropionate, methyl 2-bromoacetate, methyl 2-chloro-2-methylpropionate, methyl 2-bromo-2-methylpropionate, ethyl 2-chloroacetate, ethyl 2-bromoacetate, ethyl 2-chloropropionate, ethyl 2-bromoethanoate, ethyl 2-chloro-2-ethylpropionate, ethyl 2-bromo-2-ethylpropionate, 2-chloroacetonitrile, 2-bromoacetonitrile, 2-chloropropionitrile, 2-bromopropionitrile, 2-chloro-2-methylpropionitrile, 2-bromo-2-methylpropionitrile, (1-bromoethyl)benzene, ethyl-2-bromo-isobutyrate, 1-(1-bromoethyl)-4-chlorobenzene, 1-(1-bromoethyl)-4-trifluoromethylbenzene, 1-(1-bromoethyl)-3,5-bis-trifluoromethylbenzene, 1,2,3,4,5-pentafluoro-6-(1-bromoethyl)benzene, 1-(1-bromoethyl)-4-methoxybenzene, ethyl-2-bromo-isobutyrate, etc.

Examples of compounds represented by the formula (5) are as follows

Examples of groups represented by $R^3$, $R^4$ and $R^5$ are as given above.

Examples of compounds usable are those wherein halogen atom is replaced by hydrogen atom in the compound represented by the formula (4).

Next, a detailed description will be given of the process for preparing the compound (I).

(A) Process of Using the Compound (3) and the Compound (5):

The compound (5) is dissolved in a solvent. Examples of solvents usable are N,N-dimethylformamide (DMF), dialkyl ether, tetrahydrofuran (THF), dimethoxyethane and like ethers, toluene, xylene and like aromatic solvents, hexane and like aliphatic hydrocarbons. THF is preferable. The amount of solvent to be used, which is suitably adjusted, is 1 to 100 ml, preferably 5 to 20 ml, per gram of the compound (5).

To the solution is slowly added dropwise lithium diisopropylamide (LDA), lithium hexamethyldisilazide, lithium 2,2,6,6-tetramethylpiperizide or like lithium amide compound, potassium diisopropylamide, potassium hexamethyldisilazide, potassium 2,2,6,6-tetramethylpiperizide, potassium amide ($KNH_2$) or like potassium amide compound, or sodium amide, followed by stirring. The reaction time differs with the reaction temperature and pressure and is usually 5 minutes to 24 hours, preferably 10 minutes to 2 hours. The reaction temperature is −150° C. to 80° C., preferably −100° C. to 80° C., more preferably −78° C. to 80° C., most preferably −78° C. to 20° C. The reaction is carried out usually under atmospheric pressure, but may be carried out at increased pressure or in a vacuum. Next, a compound (3) is added to the reaction mixture, followed by stirring. The reaction time differs with the reaction temperature and pressure and is usually 5 minutes to 24 hours, preferably 10 minutes to 2 hours. The reaction temperature is −78° C. to 80° C., preferably −78° C. to 20° C., more preferably −50° C. to 20° C. The reaction is carried out usually under atmospheric pressure, but may be carried out at increased pressure or in a vacuum. The order of the compounds to be added may be changed suitably depending on the desired compound.

The proportion of the compound (5) to the compound (3) is 0.5 to 1.5 moles, preferably 0.8 to 1.2 moles of the compound (5), per mole of the compound (3).

After the completion of the reaction, the solvent is concentrated, and the desired compound is isolated and purified. Although the method of purification can be determined suitably depending on the compound, usually vacuum distillation or recrystallization is preferable.

(B) Process of Using the Compound (3) and the Compound (4):

The compound (3) is dissolved in a solvent. Examples of solvents usable are liquid ammonia, mixed solvent of liquid ammonia and tetrahydrofuran, mixed solvent of liquid ammonia and ether, mixed solvent of liquid ammonia and 1,4-dioxane or the like. The amount of solvent to be used, which is suitably adjusted, is 1 to 100 ml, preferably 5 to 20 ml, per gram of the compound (3).

To the solution is slowly added dropwise metal magnesium, metal sodium, metal potassium, metal lithium, sodium bromide, ammonium bromide or the like, followed by stirring. The reaction temperature is −78° C. to 30° C., preferably −78° C. to 0° C. The reaction is carried out usually under atmospheric pressure, but may be carried out at increased pressure or in a vacuum. The order of the compounds to be added may be changed suitably depending on the desired compound.

Next, a compound (4) is added to the reaction mixture, followed by stirring. The reaction time differs with the reaction temperature and pressure and is usually 5 minutes to 24 hours, preferably 10 minutes to 2 hours. The reaction temperature is −78° C. to 30° C., preferably −78° C. to 0° C. The reaction is carried out usually under atmospheric pressure, but may be carried out at increased pressure or in a vacuum.

The proportion of the compound (4) to the compound (3) is 0.5 to 1.5 moles, preferably 0.8 to 1.2 moles of the compound (4), per mole of the compound (3). After the completion of the reaction, the solvent is concentrated, and the desired compound is isolated and purified. Although the method of purification can be determined suitably depending on the compound, usually vacuum distillation or recrystallization is preferable.

A living radical polymerization initiator of the present invention is represented by the formula (2)

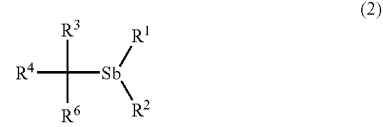

(2)

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, acyl, oxycarbonyl or cyano.

Examples of groups represented by $R^1$ to $R^4$ are as given above. Examples of groups represented by $R^6$ are those given in $R^5$ and acyl group.

Examples of acyl groups usable are formyl, acetyl and benzoyl.

An azo type polymerization initiator used in the present invention is not particularly limited insofar as it is usable in a usual radical polymerization. Example thereof are 2,2'-azobis-isobutyronitrile (AIBN), 2,2'-azobis(2-methylbutyronitrile) (AMBN), 2,2'-azobis(2,4-dimethylvaleronitrile) (ADVN), 1,1'-azobis(1-cyclohexanecarbonitrile) (ACHN), dimethyl-2,2'-azobisisobutyrate (MAIB), 4,4'-azobis(4-cyanovaleric acid) (ACVA), 1,1'-azobis(1-acetoxy-1-phenylethane), 2,2'-azobis(2-methylbutylamide), 2,2'-azobis(4-methoxy-2,4-dimethylvaleronitrile), 2,2'-azobis(2-methylamidinopropane) dihydrochloride, 2,2'-azobis[2-(2-imidazoline-2-yl)propane], 2,2'-azobis[2-methyl-N-(2-hydroxyethyl)propionamide], 2,2'-azobis(2,4,4-trimethylpentane), 2-cyano-2-propylazoformamide, 2,2'-azobis(N-butyl-2-methylpropionamide) and 2,2'-azobis(N-cyclohexyl-2-methylpropionamide).

These azo type polymerization initiators are preferably selected depending on the reaction conditions. For example, in case of low temperature polymerization, preferable are 2,2'-azobis(2,4-dimethylvaleronitrile) (ADVN) and 2,21-azobis(4-methoxy-2,4-dimethylvaleronitrile). In case of middle temperature polymerization, preferable are 2,2'-azobis-isobutyronitrile (AIBN), 2,2'-azobis(2-methylbutyronitrile) (AMBN), dimethyl-2,2'-azobisisobutyrate (MAIB) and 1,1'-azobis(1-acetoxy-1-phenylethane). In case of high temperature polymerization, preferable are 1,1'-azobis(1-cyclohexanecarbonitrile) (ACHN), 2-cyano-2-propylazoformamide, 2,2'-azobis(N-butyl-2-methylpropionamide), 2,2'-azobis(N-cyclohexyl-2-methylpropionamide) and 2,2'-azobis(2,4,4-trimethylpentane). In case of using aqueous solvent, preferable are 4,4'-azobis(4-cyanovaleric acid) (ACVA), 2,2'-azobis(2-methylbutylamide), 2,2'-azobis(2-methylamidinopropane) dihydrochloride, 2,2'-azobis[2-(2-imidazoline-2-yl)propane] and 2,2'-azobis[2-methyl-N-(2-hydroxyethyl)propionamide].

The vinyl monomer to be used in the present invention is not particularly limited insofar as the monomer can be subjected to radical polymerization. Examples of vinyl monomers usable are as follows.

Methyl (meth)acrylate, ethyl (meth)acrylate, propyl (meth)acrylate, butyl (meth)acrylate, octyl (meth)acrylate, lauryl (meth)acrylate, (meth)acrylic acid 2-hydroxyethyl ester and like (meth)acrylic acid esters, cyclohexyl (meth)acrylate, methylcyclohexyl (meth)acrylate, isobornyl (meth)acrylate, cyclododecyl (meth)acrylate and like cycloalkyl-containing unsaturated monomers.

(Meth)acrylic acid, maleic acid, fumaric acid, itaconic acid, citraconic acid, crotonic acid, maleic anhydride, methyl and like carboxyl-containing unsaturated monomers.

N,N-Dimethylaminopropyl(meth)acrylamide, N,N-dimethylaminoethyl(meth)acrylamide, 2-(dimethylamino)ethyl (meth)acrylate, N,N-dimethylaminopropyl (meth)acrylate and like unsaturated monomers containing a tertiary amine.

N-2-Hydroxy-3-acryloyloxypropyl-N,N,N-trimethylammonium chloride, N-methacryloylaminoethyl-N,N,N-dimethylbenzylammonium chloride and like unsaturated monomers containing quaternary ammonium base.

Glycidyl (meth)acrylate and like epoxy-containing unsaturated monomers.

Styrene, α-methylstyrene, 4-methylstyrene (p-methylstyrene), 2-methylstyrene (o-methylstyrene), 3-methylstyrene (m-methylstyrene), 4-methoxystyrene (p-methoxystyrene), p-t-butylstyrene, p-n-butylstyrene, p-tert-butoxystyrene, 2-hydroxymethylstyrene, 2-chlorostyrene (o-chlorostyrene), 4-chlorostyrene (p-chlorostyrene), 2,4-dichlorostyrene, 1-vinylnaphthalene, divinylbenzene, p-styrenesulfonic acid or an alkali metal salt thereof (sodium salt or potassium salt, etc.) and like aromatic unsaturated monomers (styrene type monomer).

2-Vinylthiophene, N-methyl-2-vinylpyrrole, 1-vinyl-2-pyrrolidone, 2-vinylpyridine, 4-vinylpyridine and like unsaturated monomers containing a heterocyclic ring.

N-Vinylformaldehyde, N-vinylacetamide and like vinylamides.

(Meth)acrylamide, N-methyl(meth)acrylamide, N-isopropyl-(meth)acrylamide, N,N-dimethyl(meth)acrylamide, sodium 2-acrylamide-2-methylpropanesulfonate, 6-acrylamide hexanoic acid and like (meth)acrylamide type monomers.

1-Hexene, 1-octene, 1-decene and like α-olefins.

Butadiene, isoprene, 4-methyl-1,4-hexadiene, 7-methyl-1,6-octadiene and like dienes.

Vinyl acetate, vinyl benzoate and like vinyl carboxylate.

Hydroxyethyl (meth)acrylate, (meth)acrylonitrile, methyl vinyl ketone, vinyl chloride, vinylidene chloride.

Preferable among these are (meth)acrylic acid ester, unsaturated monomers containing a cycloalkyl group, aromatic unsaturated monomers (styrene type monomers), (meth)acrylamide type monomers, (meth)acrylonitrile and methyl vinyl ketone.

Examples of preferable (meth)acrylic acid ester monomers are methyl (meth)acrylate, ethyl (meth)acrylate, propyl (meth)acrylate, butyl (meth)acrylate and (meth)acrylic acid 2-hydroxyethyl ester. Especially preferable are methyl methacrylate, ethyl methacrylate, propyl methacrylate, butyl methacrylate and methacrylic acid 2-hydroxyethyl ester.

Examples of preferable unsaturated monomers containing a cycloalkyl group are cyclohexyl (meth)acrylate and isobornyl (meth)acrylate. Especially preferable are cyclohexyl methacrylate and isobornyl methacrylate.

Examples of preferable styrene type monomers are styrene, α-methylstyrene, o-methylstyrene, p-methylstyrene, p-methoxystyrene, p-t-butylstyrene, p-n-butylstyrene, p-tert-butylstyrene, p-chlorostyrene, and p-styrenesulfonic acid or an alkali metal salt thereof (sodium salt or potassium salt, etc.). More preferable are styrene and p-chlorostyrene.

Example of preferable (meth)acrylamide type monomers is N-isopropyl-(meth)acrylamide. Especially preferable is N-isopropyl-methacrylamide.

The term "(meth)acrylic acid" refers collectively to "acrylic acid" and "methacrylic acid."

Also useful are vinyl monomers of the formula (6)

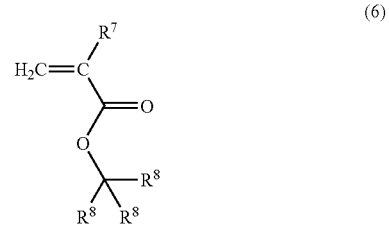

(6)

wherein $R^7$ is hydrogen, methyl, trifluoromethyl or hydroxymethyl, and the groups $R^8$ are each independently of the other a monovalent alicyclic hydrocarbon group having 4 to 20 carbon atoms or a derivative thereof, or straight-chain or branched alkyl having 1 to 4 carbon atoms, at least one of the groups $R^8$ is the alicyclic hydrocarbon group or a derivative thereof, or two of the groups $R^8$, when taken together with the carbon atom to which they are attached, form a bivalent alicyclic hydrocarbon group having 4 to 20 carbon atoms or a derivative thereof, and the remaining group or groups $R^8$ being straight-chain or branched alkyl having 1 to 4 carbon atoms or a monovalent alicyclic hydrocarbon group having 4 to 20 carbon atoms or a derivative thereof.

Examples of monovalent alicyclic hydrocarbon groups having 4 to 20 carbon atoms or derivatives thereof represented by $R^8$, examples of alicyclic hydrocarbon groups or derivatives thereof represented by at least one of the groups $R^8$, or examples of bivalent alicyclic hydrocarbon groups having 4 to 20 carbon atoms or derivatives thereof and represented by two of the groups $R^8$ as taken together with the carbon atom to which they are attached are groups comprising an alicyclic ring and derived from cycloalkanes such as bicyclo[2.2.1]heptane, tricyclo[5.2.1.0$^{2.6}$]decane, tetracyclo[6.2.1.1$^{3.6}$.0$^{2.7}$]dodecane, adamantane, cyclopentane and cyclohexane; and groups comprising such an alicyclic ring and substituted with at least one kind of or at least one of straight-chain, branched or cyclic alkyl groups having 1 to 4 carbon atoms, such as methyl, ethyl, n-propyl, i-propyl, n-butyl, 2-methylpropyl, 1-methylpropyl and tert-butyl.

Examples of derivatives of monovalent or bivalent alicyclic hydrocarbon groups represented by $R^8$ are groups having at least one kind of or at least one of substituents including hydroxyl; carboxyl; oxo (i.e., the group =O); hydroxyalkyl groups having 1 to 4 carbon atoms, such as hydroxymethyl, 1-hydroxyethyl, 2-hydroxyethyl, 1-hydroxypropyl, 2-hydroxypropyl, 3-hydroxypropyl, 2-hydroxybutyl, 3-hydroxybutyl and 4-hydroxybutyl; alkoxyl groups having 1 to 4 carbon atoms, such as methoxy, ethoxy, n-propoxy, i-propoxy, n-butoxy, 2-methylpropoxy, 1-methylpropoxy and tert-butoxy; cyano; and cyanoalkyl groups having 2 to 4 carbon atoms, such as cyanomethyl, 2-cyanomethyl, 3-cyanopropyl and 4-cyanobutyl. Preferable among these substituents are hydroxyl, carboxyl, hydroxymethyl, cyano, cyanomethyl, etc.

Examples of straight-chain or branched alkyl groups having 1 to 4 carbon atoms and represented by $R^8$ are methyl, ethyl, n-propyl, i-propyl, n-butyl, 2-methylpropyl, 1-methylpropyl, tert-butyl, etc. Preferable among these alkyl groups are methyl, ethyl, n-propyl and i-propyl.

Given below are examples of preferred functional group side chains forming —$C(R^8)_3$ in the formula (6).

1-Methyl-1-cyclopentyl, 1-ethyl-1-cyclopentyl, 1-methyl-1-cyclohexyl, 1-ethyl-1-cyclohexyl, 2-methyladamantane-2-yl, 2-methyl-3-hydroxyadamantane-2-yl, 2-ethyladamantane-2-yl, 2-ethyl-3-hydroxyadamantane-2-yl, 2-n-propyladamantane-2-yl, 2-n-propyl-3-hydroxyadamantane-2-yl, 2-isopropyladamantane-2-yl, 2-isopropyl-3-hydroxyadamantane-2-yl, 2-methylbicyclo[2.2.1]hept-2-yl, 2-ethylbicyclo[2.2.1]hept-2-yl, 8-methyltricyclo[5.2.1.0$^{2,6}$]deca-8-yl, 8-ethyltricyclo[5.2.1.0$^{2,6}$]deca-8-yl, 4-methyl-tetracyclo[6.2.1.1$^{3,6}$.0$^{2,7}$]dodeca-4-yl, 4-ethyl-tetracyclo[6.2.1.1$^{3,6}$.0$^{2,7}$]dodeca-4-yl, 1-(bicyclo[2.2.1]hept-2-yl)-1-methylethyl, 1-(tricyclo[5.2.1.0$^{2,6}$]deca-8-yl)-1-methylethyl, 1-(tetracyclo[6.2.1.1$^{3,6}$.0$^{2,7}$]deca-4-yl)-1-methylethyl, 1-(adamantane-1-yl)-1-methylethyl, 1-(3-hydroxyadamantane-1-yl)-1-methylethyl, 1,1-dicyclohexylethyl, 1,1-di(bicyclo[2.2.1]hept-2-yl)ethyl, 1,1-di(tricyclo[5.2.1.0$^{2,6}$]deca-8-yl)ethyl, 1,1-di(tetracyclo[6.2.1.1$^{3,6}$.0$^{2,7}$]dodeca-4-yl)ethyl, 1,1-di(adamantane-1-yl)ethyl, etc.

Further, preferable examples of the vinyl monomers of the formula (6) are as follows.

(Meth)acrylic acid 1-methyl-1-cyclopentyl ester, (meth)acrylic acid 1-ethyl-1-cyclopentyl ester, (meth)acrylic acid 1-methyl-1-cyclohexyl ester, (meth)acrylic acid 1-ethyl-1-cyclohexyl ester, (meth)acrylic acid 2-methyladamantane-2-yl ester, (meth)acrylic acid 2-methyl 3-hydroxyadamantane-2-yl ester, (meth)acrylic acid 2-ethyladamantane-2-yl ester, (meth)acrylic acid 2-ethyl 3-hydroxyadamantane-2-yl ester, (meth)acrylic acid 2-n-propyl-adamantane-2-yl ester, (meth)acrylic acid 2-n-propyl 3-hydroxyadamantane-2-yl ester, (meth)acrylic acid 2-isopropyladamantane-2-yl ester, (meth)acrylic acid 2-isopropyl 3-hydroxyadamantane-2-yl ester, (meth)acrylic acid 2-methyladamantane-2-yl ester, (meth)acrylic acid 2-methylbicyclo[2.2.1]hept-2-yl ester, (meth)acrylic acid 2-ethylbicyclo[2.2.1]hept-2-yl ester, (meth)acrylic acid 8-methyltricyclo[5.2.1.0$^{2,6}$]deca-8-yl ester, (meth)acrylic acid 8-ethyltricyclo[5.2.1.0$^{2,6}$]deca-8-yl ester, (meth)acrylic acid 4-methyltetracyclo[6.2.1.1$^{3,6}$.0$^{2,7}$]-dodeca-4-yl ester, (meth)acrylic acid 4-ethyltetracyclo[6.2.1.1$^{3,6}$.0$^{2,7}$]dodeca-4-yl ester, (meth)acrylic acid 1-(bicyclo[2.2.1]hept-2-yl)-1-methyl ester, (meth)acrylic acid 1-(tricyclo[5.2.1.0$^{2,6}$]deca-8-yl)-1-methyl ester, (meth)acrylic acid 1-(tetracyclo[6.2.1.1$^{3,6}$.0$^{2,7}$]dodeca-4-yl)-1-methylethyl ester, (meth)acrylic acid 1-(adamantane-1-yl)-1-methylethyl ester, (meth)acrylic acid 1-(3-hydroxyadamantane-1-yl)-1-methylethyl ester, (meth)acrylic acid 1,1-dicyclohexylethyl ester, (meth)acrylic acid 1,1-di(bicyclo[2.2.1]hept-2-yl)ethyl ester, (meth)acrylic acid 1,1-di(tricyclo[5.2.1.0$^{2,6}$]deca-8-yl)ethyl ester, (meth)acrylic acid 1,1-di(tetracyclo[6.2.1.1$^{3,6}$.0$^{2,7}$]dodeca-4-yl)ethyl ester and (meth)acrylic acid 1,1-di(adamantane-1-yl)ethyl ester.

Especially preferable examples of the vinyl monomers of the formula (6) are (meth)acrylic acid 1-methyl-1-cyclopentyl ester, (meth)acrylic acid 1-ethyl-1-cyclopentyl ester, (meth)acrylic acid 1-methyl-1-cyclohexyl ester, (meth)acrylic acid 1-ethyl-1-cyclohexyl ester, (meth)acrylic acid 2-methyladamantane-2-yl ester, (meth)acrylic acid 2-ethyladamantane-2-yl ester, (meth)acrylic acid 2-n-propyladamantane-2-yl ester, (meth)acrylic acid 2-isopropyladamantane-2-yl ester and (meth)acrylic acid 1-(adamantane-1-yl)-1-methylethyl ester.

Vinyl monomers of the formulas (7) to (13) below are usable in addition to the vinyl monomers of the formula (6)

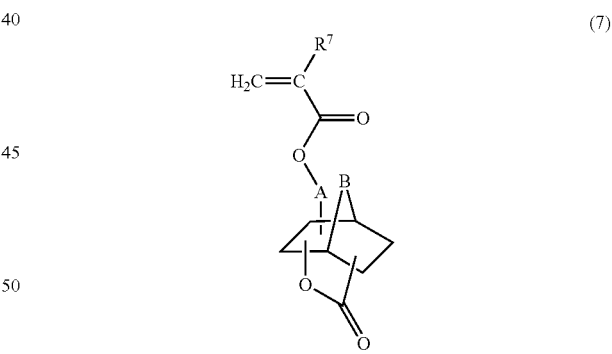

(7)

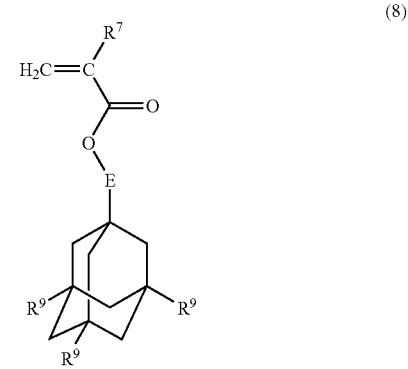

(8)

-continued

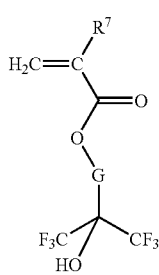
(9)

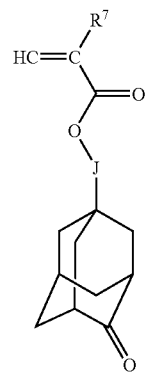
(10)

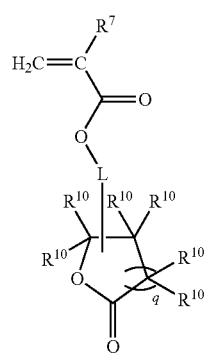
(11)

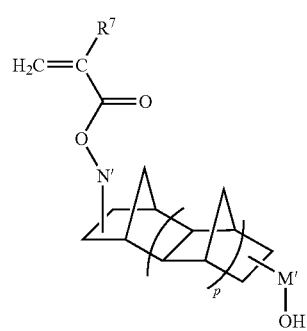
(12)

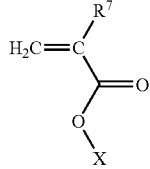
(13)

In the above formulae (7) to (13), $R^7$ is the same as the $R^7$ of the formula (6).

In the formula (7), A is a single bond, or straight-chain or branched alkylene which may have a substituent with 1 to 6 carbon atoms, or a mono- or di-alkylene glycol group or alkylene ester group. Examples of straight-chain or branched alkylene groups having 1 to 6 carbon atoms are methylene, ethylene, propylene, butylene, pentylene, hexylene and cyclohexylene. B is a single bond or alkylene which may have a substituent with 1 to 3 carbon atoms, alkyloxy or an oxygen atom.

In the formula (8), E is a single bond or bivalent alkylene having 1 to 3 carbon atoms, and the groups $R^9$ are independent of one another and are each hydroxyl, cyano, carboxyl, —COOR$^e$ or —Y—R$^d$. R$^e$ is a hydrogen atom, straight-chain or branched alkyl having 1 to 4 carbon atoms or alicyclic alkyl having 3 to 20 carbon atoms. The groups Y are independent of one another and are each a single bond or bivalent alkylene having 1 to 3 carbon atoms. The groups $R^4$ are independent of one another and are each a hydrogen atom, hydroxyl, cyano or the group —COOR$^e$. However, at least one of the groups $R^9$ is not a hydrogen atom. Examples of E and Y are a single bond, methylene, ethylene and propylene.

The group $R^e$ in —COOR$^e$ is a hydrogen atom, straight-chain or branched alkyl having 1 to 4 carbon atoms or alicyclic alkyl having 3 to 20 carbon atoms. Examples of straight-chain or branched alkyl groups having 1 to 4 carbon atoms can be methyl, ethyl, n-propyl, i-propyl, n-butyl, 2-methylpropyl, 1-methylpropyl and tert-butyl. Examples of alicyclic alkyl having 3 to 20 carbon atoms are cycloalkyl groups represented by —CnH$_{2n-1}$ (wherein n is an integer of 3 to 20), such as cyclopropyl, cyclobutyl, cyclopentyl, cyclohexyl, cycloheptyl and cyclooctyl; polycyclic alicyclic alkyl groups such as bicyclo[2.2.1]heptyl, tricyclo[5.2.1.0$^{2.6}$]decyl, tetracyclo[6.2.1$^{3.6}$.0$^{2.7}$]dodecanyl and adamantyl; or cycloalkyl groups or polycyclic alicyclic alkyl groups as partly substituted with at least one kind of or at least one of straight-chain, branched or cyclic alkyl groups.

In the formula (9), G is a single bond, straight-chain or branched alkylene having 1 to 6 carbon atoms, an alicyclic hydrocarbon group having 4 to 20 carbon atoms, alkylene glycol group or alkylene ester group. Examples of straight-chain or branched alkylene groups having 1 to 6 carbon atoms are methylene, ethylene, propylene, butylenes, pentylene, hexylene and cyclohexylene.

In the formula (10), J is a single bond, or straight-chain, branched or cyclic alkylene which may have a substituent with 1 to 20 carbon atoms, an alkylene glycol group or alkylene ester group.

In the formula (11), L is a single bond, or straight-chain, branched or cyclic alkylene which may have a substituent with 1 to 20 carbon atoms, an alkylene glycol group or alkylene ester group. $R^{10}$ is a hydrogen atom, straight-chain or branched alkyl having 1 to 4 carbon atoms, alkoxyl, hydroxyalkyl, a bivalent alicyclic hydrocarbon group having 3 to 20 carbon atoms or a group comprising a derivative thereof. q is 1 or 2.

In the formula (12), N' and M' are independent of each other and are each straight-chain, branched or cyclic alkylene which may have a substituent with 1 to 20 carbon atoms, an alkylene glycol group or alkylene ester group. Examples of straight-chain or branched alkylene groups are methylene, ethylene, propylene, butylenes, pentylene, hexylene and cyclohexylene. p is 0 or 1.

In the formula (13), X is a polycyclic alicyclic hydrocarbon group having 7 to 20 carbon atoms, containing no polar group and consisting only of carbon and hydrogen. Examples of such polycyclic alicyclic hydrocarbon groups are hydrocarbon groups comprising an alicyclic ring and derived from cycloalkanes such as bicyclo[2.2.1]heptane, bicyclo[2.2.2]octane, tricyclo[5.2.1.0$^{2.6}$]decane, tetracyclo[4.4.0.1$^{2.6}$.1$^{7.10}$]dodecane and tetracyclo[6.2.1.1$^{3.6}$.0$^{2.7}$]decane. Such alicyclic rings may have a substituent, that is, they may be substituted with at least one kind of or at least one of straight-chain or cyclic alkyl groups having 1 to 4 carbon atoms, such as methyl, ethyl, n-propyl, i-propyl, n-butyl, 2-methylpropyl, 1-methylpropyl and tert-butyl.

Examples of vinyl monomers of the formula (7) are those represented by the formulae (7-1) to (7-7) given below.

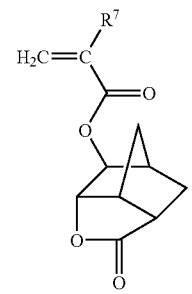
(7-1)

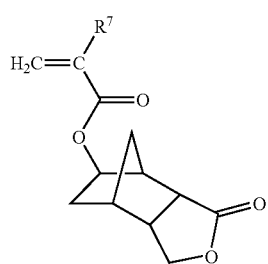
(7-2)

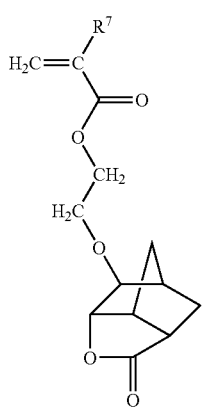
(7-3)

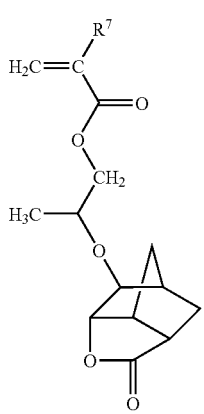
(7-4)

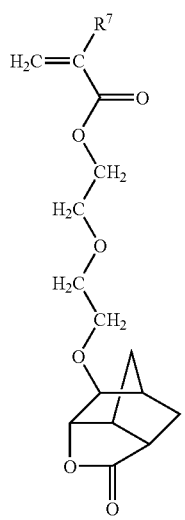
(7-5)

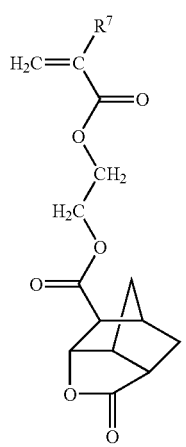
(7-6)

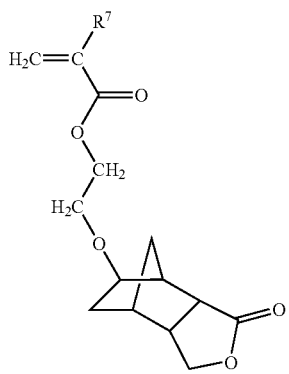
(7-7)

$R^7$ is a hydrogen atom, methyl, trifluoromethyl or hydroxymethyl. Preferable as the vinyl monomer is norbornane wherein the methylene group at the 7-position corresponding to the bridgehead is replaced by an oxygen atom.

Given below are examples of preferred vinyl monomers of the formula (8).

(Meth)acrylic acid 3-hydroxyadamantane ester, (meth)acrylic acid 3-hydroxyadamantane-1-yl methyl ester, (meth)acrylic acid 3,5-dihydroxyadamantane-1-yl methyl ester, (meth)acrylic acid 3-hydroxy-5-cyanoadamantane-1-yl methyl ester, (meth)acrylic acid 3-hydroxy-5-carboxyladamantane-1-yl methyl ester, (meth)acrylic acid 3-hydroxy-5-methoxycarbonyladamantane-1-yl methyl ester, (meth)

acrylic acid 3-hydroxymethyladamantane-1-yl methyl ester, (meth)acrylic acid 3,5-dihydroxymethyladamantane-1-yl methyl ester, (meth)acrylic acid 3-hydroxy-5-hydroxymethyladamantane-1-yl methyl ester, (meth)acrylic acid 3-cyano-5-hydroxymethyladamantane-1-yl methyl ester, (meth)acrylic acid 3-hydroxymethyl-5-carboxyladamantane-1-yl methyl ester, (meth)acrylic acid 3-hydroxymethyl-5-methoxycarbonyladamantane-1-yl methyl ester, (meth)acrylic acid 3-cyanoadamantane-1-yl methyl ester, (meth)acrylic acid 3,5-dicyanoadamantane-1-yl methyl ester, (meth)acrylic acid 3-cyano-5-carboxyladamantane-1-yl methyl ester, (meth)acrylic acid 3-cyano-5-methoxycarbonyladamantane-1-yl methyl ester, (meth)acrylic acid 3-carboxyladamantane-1-yl methyl ester, (meth)acrylic acid 3,5-dicarboxyladamantane-1-yl methyl ester, (meth)acrylic acid 3-carboxyl-5-methoxycarbonyladamantane-1-yl methyl ester, (meth)acrylic acid 3-methoxycarbonyladamantane-1-yl methyl ester, (meth)acrylic acid 3,5-dimethoxycarbonyladamantane-1-yl methyl ester, (meth)acrylic acid 3-hydroxy-5-methyladamantane-1-yl ester, (meth)acrylic acid 3,5-dihydroxy-7-methyladamantane-1-yl ester, (meth)acrylic acid 3-hydroxy-5-cyano-7-methyladamantane-1-yl ester, (meth)acrylic acid 3-hydroxy-5-carboxyl-7-methyladamantane-1-yl ester, (meth)acrylic acid 3-hydroxy-5-methoxycarbonyl-7-methyladamantane-1-yl ester, (meth)acrylic acid 3-hydroxymethyl-5-methyladamantane-1-yl ester, (meth)acrylic acid 3,5-dihydroxymethyl-7-methyladamantane-1-yl ester, (meth)acrylic acid 3-hydroxy-5-hydroxymethyl-7-methyladamantane-1-yl ester, (meth)acrylic acid 3-cyano-5-hydroxymethyl-7-methyladamantane-1-yl ester, (meth)acrylic acid 3-hydroxymethyl-5-carboxyl-7-methyladamantane-1-yl ester, (meth)acrylic acid 3-hydroxymethyl-5-methoxycarbonyl-7-methyladamantane-1-yl ester, (meth)acrylic acid 3-cyano-5-methyladamantane-1-yl ester, (meth)acrylic acid 3,5-dicyano-7-methyladamantane-1-yl ester, (meth)acrylic acid 3-cyano-5-carboxyl-7-methyladamantane-1-yl ester, (meth)acrylic acid 3-cyano-5-methoxycarbonyl-7-methyladamantane-1-yl ester, (meth)acrylic acid 3-carboxyl-5-methyladamantane-1-yl ester, (meth)acrylic acid 3,5-dicarboxyl-7-methyladamantane-1-yl ester, (meth)acrylic acid 3-carboxyl-5-methoxycarbonyl-7-methyladamantane-1-yl ester, (meth)acrylic acid 3-methoxycarboxyl-5-methyladamantane-1-yl ester, (meth)acrylic acid 3,5-dimethoxycarbonyl-7-methyladamantane-1-yl ester, (meth)acrylic acid 3-hydroxy-5-methyladamantane-1-yl methyl ester, (meth)acrylic acid 3,5-dihydroxy-7-methyladamantane-1-yl methyl ester, (meth)acrylic acid 3-hydroxy-5-cyano-7-methyladamantane-1-yl methyl ester, (meth)acrylic acid 3-hydroxy-5-carboxyl-7-methyladamantane-1-yl methyl ester, (meth)acrylic acid 3-hydroxy-5-methoxycarbonyl-7-methyladamantane-1-yl methyl ester, (meth)acrylic acid 3-hydroxymethyl-5-methyladamantane-1-yl methyl ester, (meth)acrylic acid 3,5-dihydroxymethyl-7-methyladamantane-1-yl methyl ester, (meth)acrylic acid 3-hydroxy-5-hydroxymethyl-7-methyladamantane-1-yl methyl ester, (meth)acrylic acid 3-cyano-5-hydroxymethyl-7-methyladamantane-1-yl methyl ester, (meth)acrylic acid 3-hydroxymethyl-5-carboxyl-7-methyladamantane-1-yl methyl ester, (meth)acrylic acid 3-hydroxymethyl-5-methoxycarbonyl-7-methyladamantane-1-yl methyl ester, (meth)acrylic acid 3-cyano-5-methyladamantane-1-yl methyl ester, (meth)acrylic acid 3,5-dicyano-7-methyladamantane-1-yl methyl ester, (meth)acrylic acid 3-cyano-5-carboxyl-7-methyladamantane-1-yl methyl ester, (meth)acrylic acid 3-cyano-5-methoxycarbonyl-7-methyladamantane-1-yl methyl ester, (meth)acrylic acid 3-carboxyl-5-methyladamantane-1-yl methyl ester, (meth)acrylic acid 3,5-dicarboxyl-7-methyladamantane-1-yl methyl ester, (meth)acrylic acid 3-carboxyl-5-methoxycarbonyl-7-methyladamantane-1-yl methyl ester, (meth)acrylic acid 3-methoxycarbonyl-5-methyladamantane-1-yl methyl ester, (meth)acrylic acid 3,5-dimethoxycarbonyl-7-methyladamantane-1-yl methyl ester, (meth)acrylic acid 3-hydroxy-5,7-dimethyladamantane-1-yl ester, (meth)acrylic acid 3-hydroxymethyl-5,7-dimethyladamantane-1-yl ester, (meth)acrylic acid 3-cyano-5,7-dimethyladamantane-1-yl ester, (meth)acrylic acid 3-carboxyl-5,7-dimethyladamantane-1-yl ester, (meth)acrylic acid 3-methoxycarbonyl-5,7-dimethyladamantane-1-yl ester, (meth)acrylic acid 3-hydroxy-5,7-dimethyladamantane-1-yl methyl ester, (meth)acrylic acid 3-hydroxymethyl-5,7-dimethyladamantane-1-yl methyl ester, (meth)acrylic acid 3-cyano-5,7-dimethyladamantane-1-yl methyl ester, (meth)acrylic acid 3-carboxyl-5,7-dimethyladamantane-1-yl methyl ester, (meth)acrylic acid 3-methoxycarbonyl-5,7-dimethyladamantane-1-yl methyl ester, etc.

Among the vinyl monomers of the formula (8), especially preferable are (meth)acrylic acid 3-hydroxyadamantane-1-yl ester, (meth)acrylic acid 3-hydroxyadamantane-1-yl methyl ester, (meth)acrylic acid 3,5-dihydroxyadamantane-1-yl methyl ester, (meth)acrylic acid 3-cyanoadamantane-1-yl methyl ester, (meth)acrylic acid 3-carboxyladamantane-1-yl methyl ester, (meth)acrylic acid 3-hydroxy-5-methyladamantane-1-yl ester, (meth)acrylic acid 3,5-dihydroxy-7-methyladamantane-1-yl ester, (meth)acrylic acid 3-hydroxy-5,7-dimethyladamantane-1-yl ester, (meth)acrylic acid 3-carboxyl-5,7-dimethyladamantane-1-yl ester and (meth)acrylic acid 3-hydroxy-5,7-dimethyladamantane-1-yl methyl ester, etc.

Among the vinyl monomers of the formula (9), especially preferable are those of the formulas (9-1) to (9-8) below.

(9-1)

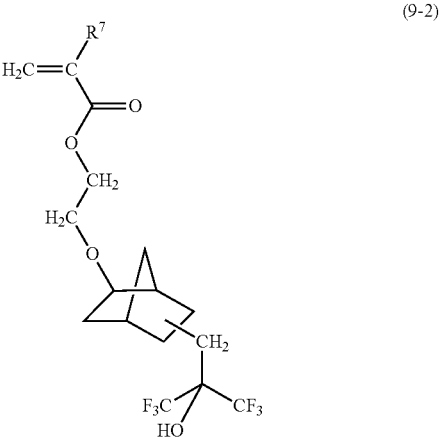

(9-2)

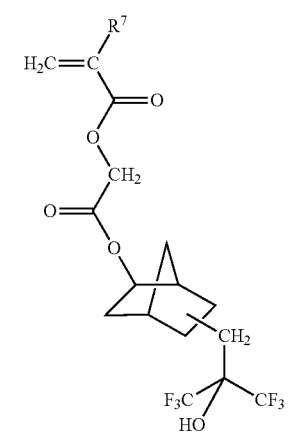
(9-3)
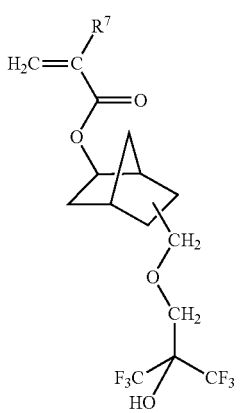
(9-4)
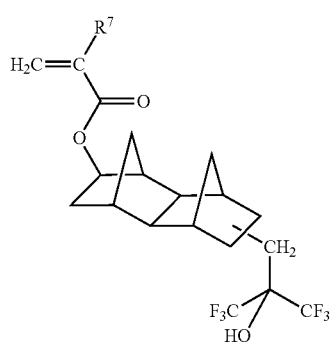
(9-5)
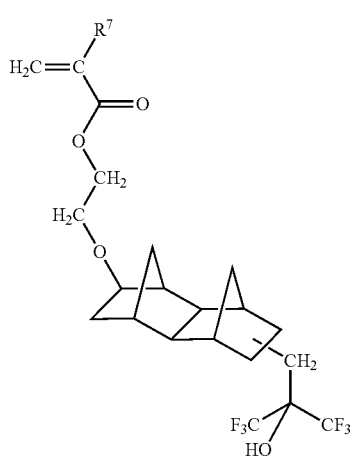
(9-6)
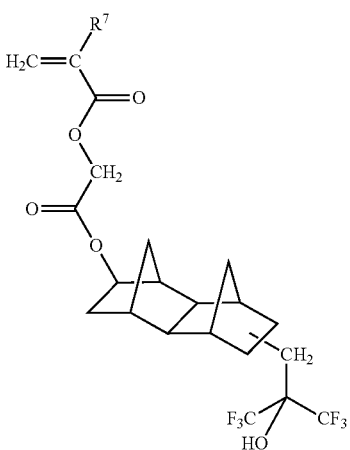
(9-7)
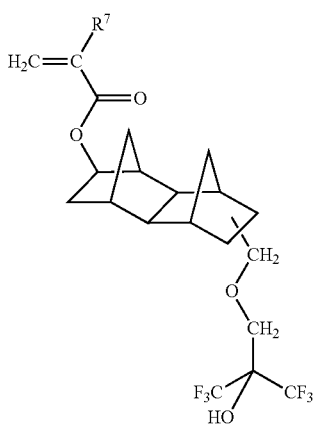
(9-8)
In the above formulae, $R^7$ is a hydrogen atom, methyl, trifluoromethyl or hydroxymethyl. Preferable as the vinyl monomer is norbornane wherein the methylene group at the 7-position corresponding to the bridgehead is replaced by an oxygen atom.
Among the vinyl monomers of the formula (10), especially preferable are those of the formulas (10-1) to (10-4) below.
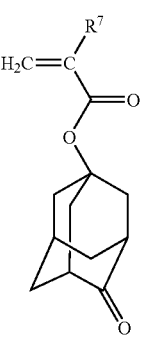
(10-1)

-continued
(10-2)
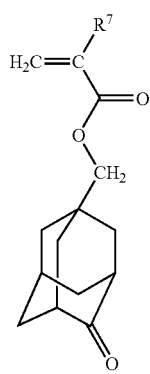
(10-3)
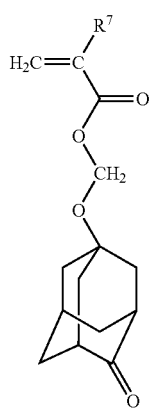
(10-4)
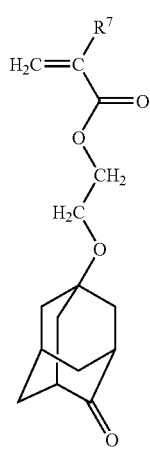
In the above, $R^7$ is a hydrogen atom, methyl, trifluoromethyl or hydroxymethyl.
Among the vinyl monomers of the formula (11), especially preferable are those of the formulas (11-1) to (11-15) below.
(11-1)
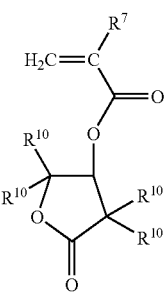
(11-2)
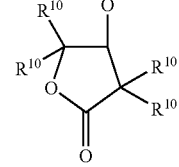
(11-3)
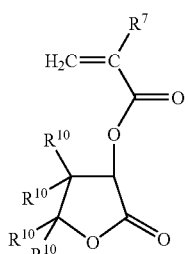
(11-4)
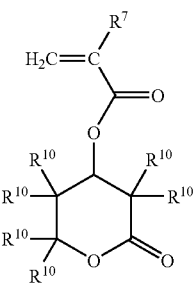
(11-5)
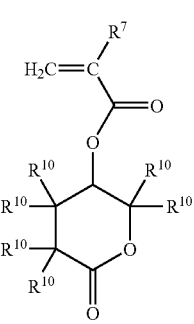

(11-6)
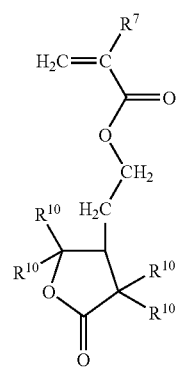
(11-7)
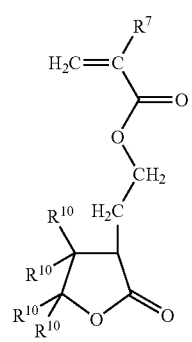
(11-8)
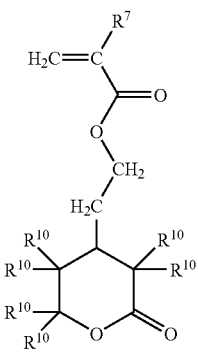
(11-9)
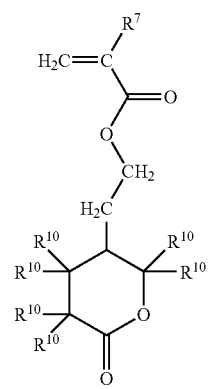
(11-10)
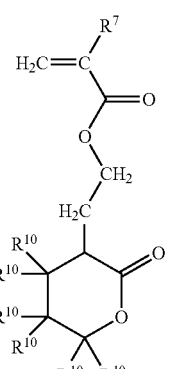
(11-11)
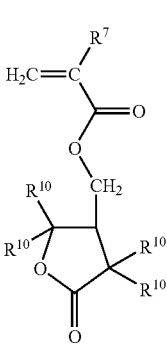
(11-12)
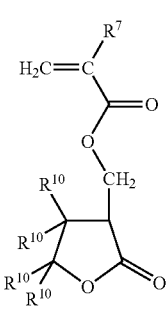
(11-13)
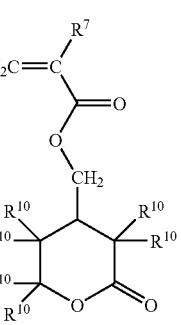

(11-14)
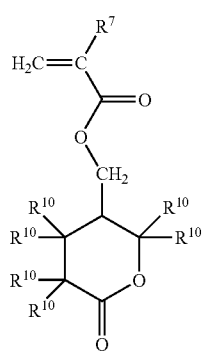
(11-15)
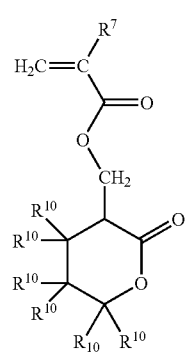
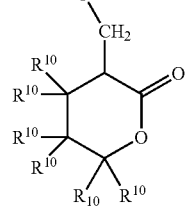
In the above, preferable examples of $R^{10}$ are a hydrogen atom, methyl, ethyl, propyl, butyl, cyclohexyl, norbornyl, adamantly, methoxy, ethoxy, propoxy, butoxy, hydroxymethyl and hydroxyethyl.
Among the vinyl monomers of the formula (12), especially preferable are those of the formulas (12-1) to (12-12) below.
(12-1)
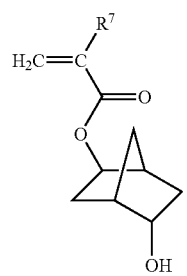
(12-2)
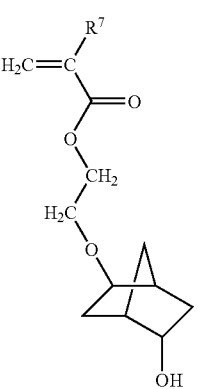
(12-3)
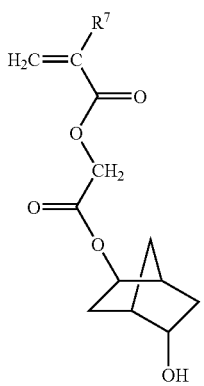
(12-4)
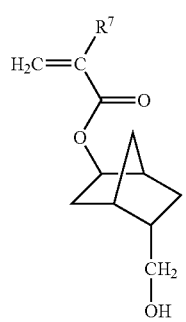
(12-5)
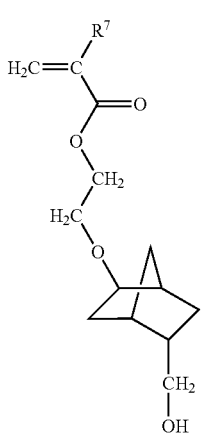
(12-6)
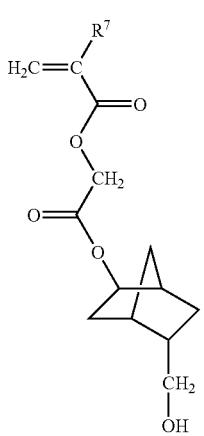

(12-7)
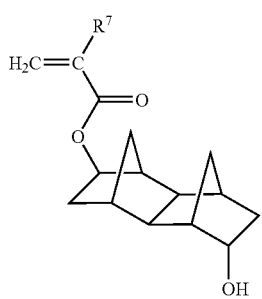
(12-8)
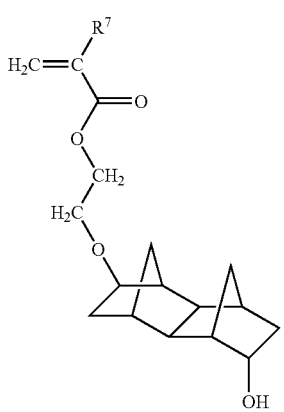
(12-9)
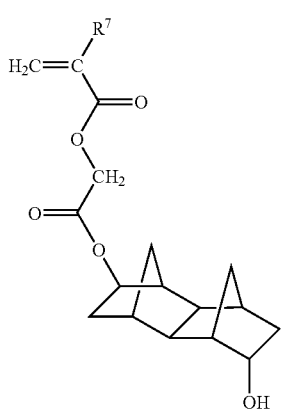
(12-10)
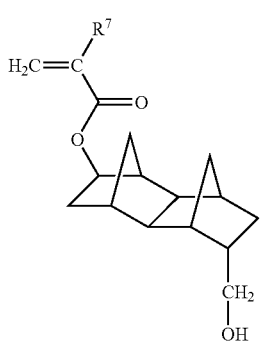
(12-11)
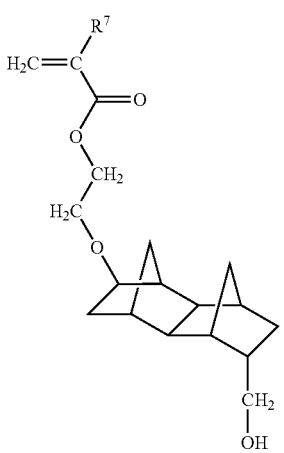
(12-12)
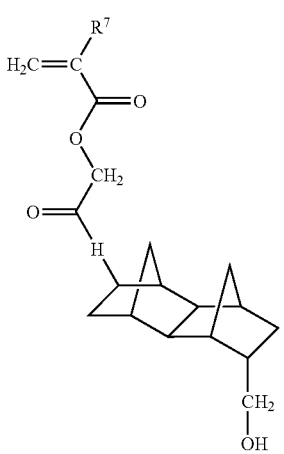
Among the vinyl monomers of the formula (13) especially preferable are those of the formulas (13-1) to (13-12) below. These monomers can be usable singly or at least two of them can be usable in mixture.
(13-1)
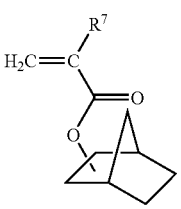
(13-2)
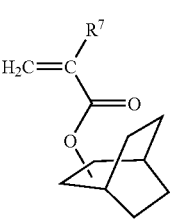

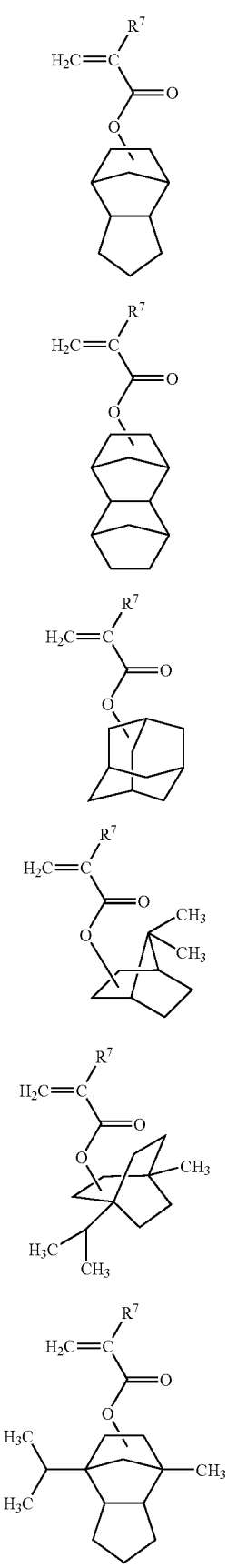

(13-3)
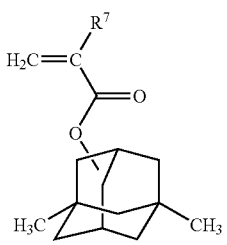

(13-4)
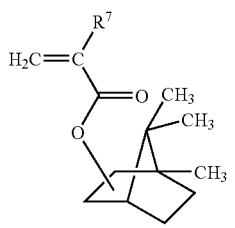

(13-9)

(13-10)
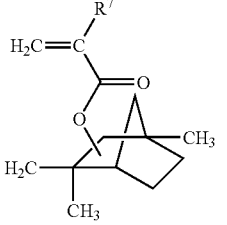

(13-11)
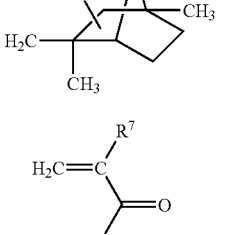

(13-5)

(13-12)
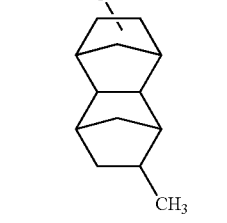

(13-6)

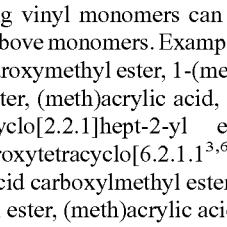

(13-7)

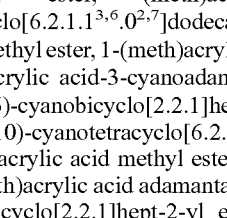

(13-8)

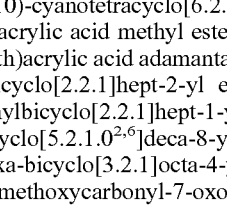

The following vinyl monomers can be further usable in addition to the above monomers. Examples thereof are (meth) acrylic acid hydroxymethyl ester, 1-(meth)acrylic acid-2-hydroxymethyl ester, (meth)acrylic acid, (meth)acyclic acid-5 (6)-hydroxybicyclo[2.2.1]hept-2-yl ester, (meth)acrylic acid-9(10)-hydroxytetracyclo[6.2.1.1$^{3,6}$.0$^{2,7}$]dodeca-4-yl, (meth)acrylic acid carboxylmethyl ester, (meth)acrylic acid-2-carboxylethyl ester, (meth)acrylic acid-3-carboxyadamantane-1-yl ester, (meth)acrylic acid 5(6)-carboxybicyclo [2.2.1]hept-2-yl ester, (meth)acrylic acid-9(10)-carboxytetracyclo[6.2.1.1$^{3,6}$.0$^{2,7}$]dodeca-4-yl ester, (meth) acrylic cyanomethyl ester, 1-(meth)acrylic acid-2-cyanoethyl ester, (meth) acrylic acid-3-cyanoadamantane-1-yl, (meth) acrylic acid-5(6)-cyanobicyclo[2.2.1]hept-2-yl ester, (meth) acrylic acid-9(10)-cyanotetracyclo[6.2.1.1$^{3,6}$.0$^{2,7}$]dodeca-4-yl ester, (meth)acrylic acid methyl ester, (meth)acrylic acid ethyl ester, (meth)acrylic acid adamantane-1-yl ester, (meth) acrylic acid bicyclo[2.2.1]hept-2-yl ester, (meth) acrylic acid-7,7-dimethylbicyclo[2.2.1]hept-1-yl ester, (meth) acrylic acid tricyclo[5.2.1.0$^{2,6}$]deca-8-yl ester, (meth)acrylic acid-7-oxo-6-oxa-bicyclo[3.2.1]octa-4-yl ester, (meth) acrylic acid-2-methoxycarbonyl-7-oxo-6-oxabicyclo[3.2.1]

octa-4-yl ester, (meth)acrylic acid-2-oxotetrahydropyran-4-yl ester, (meth)acrylic acid-4-methyl-2-oxotetrahydropyran-4-yl ester, (meth)acrylic acid-5-oxotetrahydropyran-3-yl ester, (meth)acrylic acid-2,2-dimethyl-5-oxotetrahydrofuran-3-yl ester, (meth)acrylic acid-4,4-dimethyl-5-oxotetrahydrofuran-3-yl ester, (meth)acrylic acid-2-oxotetrahydrofuran-3-yl ester, (meth)acrylic acid-4,4-dimethyl-2-oxotetrahydrofuran-3-yl ester, (meth)acrylic acid-5,5-dimethyl-2-oxotetrahydrofuran-3-yl ester, (meth)acrylic acid-5-oxotetrahydrofuran-2-yl methyl ester, (meth)acrylic acid-3,3-dimethyl-5-oxotetrahydrofuran-2-yl methyl ester, N,N-dimethyl (meth)acryl amide, crotonic amide, maleic amide, fumaric amide, mesaconic amide, citraconic amide, itaconic amide, etc.; methylene glycol di(meth)acrylate, ethylene glycol di(meth)acrylate, 2,5-dimethyl-2,5-hexanediol di(meth)acrylate, 1,2-adamantanediol di(meth)acrylate, 1,3-adamantanediol di(meth)acrylate, 1,4-adamantanediol di(meth)acrylate, tricyclodecanyldimethyloldi(meth)acrylate, etc.

The resin containing an acid-dissociable group and precision-controlled in molecular weight and molecular weight distribution (PD=Mw/Mn) can be prepared within a short period of time in a high yield by polymerizing at least one of vinyl monomers of the formula (6) to the formula (13) using a living radical polymerization initiator of the invention represented by the formula (2).

Specifically stated, the living radical polymer of the present invention is produced by the process to be described below.

A vinyl monomer, a living radical polymerization initiator of the formula (2), and as required an azo type polymerization initiator are mixed together in a container having its inside air replaced by an inert gas. Next, the mixture is then stirred. The reaction temperature and the reaction time may be adjusted suitably. The mixture is stirred usually at 20 to 150° C. for 1 minute to 100 hours, preferably at 40 to 100° C. for 0.1 to 30 hours. The reaction is carried out usually under atmospheric pressure, but may be carried out at increased pressure or in a vacuum. Examples of inert gases usable at this time are nitrogen, argon, helium, etc., among which argon and nitrogen are preferred. Nitrogen is especially preferred.

Although the vinyl monomer and the living radical polymerization initiator of the formula (2) are used in amounts which are suitably adjusted depending on the molecular weight and molecular weight distribution of the living radical polymer to be obtained, usually 5 to 10,000 moles, preferably 50 to 5,000 moles, of the vinyl monomer is used per mole of the living radical polymerization initiator of the formula (2).

In case of combined use of the living radical polymerization initiator of the formula (2) and the azo type polymerization initiator, the latter is used in the ratio of usually 0.01 to 100 moles, preferably 0.1 to 10 moles, especially preferably 0.1 to 5 moles, per mole of the former. The vinyl monomer is used in an amount of 5 to 10,000 moles, preferably 50 to 5,000 moles, per mole of the living radical polymerization initiator of the formula (2).

The polymerization reaction is carried out usually in the absence of solvent, while an organic solvent generally in use for radical polymerization or an aqueous solvent may be used. Examples of organic solvents usable are benzene, toluene, N,N-dimethylformamide (DMF), dimethyl sulfoxide (DMSO), acetone, 2-butanone (methyl ethyl ketone), dioxane, hexafluoroisopropanol, chloroform, carbon tetrachloride, tetrahydrofuran (THF), ethyl acetate, trifluoromethylbenzene, etc. Examples of aqueous solvents are water, methanol, ethanol, isopropanol, n-butanol, ethyl cellosolve, butyl cellosolve, 1-methoxy-2-propanol, diacetonealcohol, etc. The amount of the solvent to be used is adjusted suitably. For example, 0.01 to 50 ml, preferably 0.05 to 10 ml, more preferably 0.1 to 1 ml, of the solvent is used per gram of the vinyl monomer.

Next, the mixture is then stirred. The reaction temperature and the reaction time may be adjusted suitably in accordance with the molecular weight or molecular weight distribution of the living radical polymer to be obtained. The mixture is stirred usually at 20 to 150° C. for 1 minute to 100 hours, preferably at 40 to 100° C. for 0.1 to 30 hours. The mixture is stirred more preferably at 40 to 80° C. for 0.1 to 15 hours. Thus, the present invention has a feature that a high yield and precise PD are performed even at such a low polymerization temperature and short period of polymerization time. The reaction is carried out usually under atmospheric pressure, but may be carried out at increased pressure or in a vacuum.

After the completion of the reaction, the solvent used and the remaining monomer are removed in a vacuum to take out the desired polymer, or the desired product is isolated by re-precipitation using a solvent wherein the product is insoluble. The reaction mixture can be treated by any method insofar as it causes no problem to the desired product.

According to the invention, it is possible to use the emulsion polymerization process wherein a surfactant is used to carry out polymerization mainly in a micelle. When required, a dispersant of water-soluble high polymer, such as a polyvinyl alcohol, may be used. Such surfactants are usable singly, or at least two of them can be used in combination. The surfactant is used preferably in an amount of 0.3 to 50 parts by weight, more preferably 0.5 to 50 parts by weight, per 100 parts by weight of all monomers. Water is used preferably in an amount of 50 to 2000 parts by weight, more preferably 70 to 1500 parts by weight, per 100 parts by weight of all monomers. The polymerization temperature is preferably in the range of 0 to 100° C., more preferably 40 to 90° C., although not limited particularly. The reaction time is suitably determined so as to complete the polymerization reaction, for example, in accordance with the reaction temperature, or with the monomer composition to be used and the kind of surfactant and polymerization initiator. The reaction time is preferably within 24 hours.

According to the invention, the suspension polymerization process is also usable in which a dispersant is used to conduct polymerization generally without using any micelle. Also usable along with the dispersant are auxiliary dispersants such as sodium chloride, potassium chloride, sodium sulfate, potassium sulfate and manganese sulfate when so required. Such stabilizers for dispersion in water are used preferably in an amount of 0.01 to 30 parts by weight, more preferably 0.05 to 10 parts by weight, and most preferably 0.1 to 5 parts by weight, per 100 parts by weight of the monomers. Water is used preferably in an amount of 50 to 2000 parts by weight, more preferably 70 to 1500 parts by weight, per 100 parts by weight of the monomers. The polymerization temperature is preferably in the range of 0 to 100° C., more preferably 40 to 90° C., although not limited particularly. The reaction time is suitably determined so as to complete the polymerization reaction, for example, in accordance with the reaction temperature, or with the monomer composition to be used and the kind of water dispersion stabilizer and polymerization initiator. The reaction time is preferably within 24 hours.

The miniemulsion polymerization process is further usable according to the invention. The monomer is forcibly dispersed using a surfactant and cosurfactant and also using a homogenizer or ultrasonic device, but generally without using any micelle. Such surfactant and cosurfactant are used in an amount of 0.3 to 50 parts by weight, preferably 0.5 to 50 parts, based on the monomers. The ultrasonic irradiation time is 0.1 to 10 minutes, preferably 0.2 to 5 minutes.

According to the present invention, at least one compound selected from among a ditelluride compound, distibine compound and dibismuthine compound can be admixed with the living radical polymerization initiator of the formula (2), or with a mixture of this initiator and an azo polymerization initiator as required, for the polymerization of the vinyl monomer. Stated more specifically, the present invention provides, for example, a process for preparing a living radical polymer by polymerizing the vinyl monomer using a mixture of the living radical polymerization initiator of the formula (2) and at least one compound selected from among a ditelluride compound, distibine compound and dibismuthine compound, and a process for preparing a living radical polymer by polymerizing the vinyl monomer using a mixture of the living radical polymerization initiator of the formula (2), an azo polymerization initiator and at least one compound selected from among a ditelluride compound, distibine compound and dibismuthine compound.

The ditelluride compound to be used in the present invention can be a known ditelluride compound or one prepared by a common process. Examples of preparation processes are those disclosed in WO2004-014962 and WO2004-096870.

Examples of ditelluride compounds are dimethyl ditelluride, diethyl ditelluride, di-n-propyl ditelluride, diisopropyl ditelluride, dicyclopropyl ditelluride, di-n-butyl ditelluride, di-sec-butyl ditelluride, di-tert-butyl ditelluride, dicyclobutyl ditelluride, diphenyl ditelluride, bis(p-methoxyphenyl) ditelluride, bis(p-aminophenyl) ditelluride, bis(p-nitrophenyl) ditelluride, bis(p-cyanophenyl) ditelluride, bis(p-sulfonylphenyl) ditelluride, dinaphthyl ditelluride, dipyridyl ditelluride, etc.

The distibine compound to be used in the present invention can be a known distibine compound or one prepared by a common process. Examples of preparation processes are those disclosed in J. Organomet. Chem., 1973, Vol. 51, p. 223; Organometallics, 1982, Vol. 1, p. 1408; and Organometallics, 1983, Vol. 2, p. 1859.

Examples of distibine compounds are tetramethyldistibine, tetraethyldistibine, tetraisopropyldistibine, tetrabutyldistibine, tetravinyldistibine, tetraisopropenyldistibine, tetraisobutenyldistibine, tetraphenyldistibine, tetrakis(trimethylsilyl)distibine, 1,1'-bistibolane, tetramethyldistiboryl, etc.

The dibismuthine compound to be used in the present invention can be a known dibismuthine compound or one prepared by a common process. Examples of preparation processes are those disclosed in Chem. Z., 1977, Vol. 101, p. 399; and J. Organomet. Chem., 1980, Vol. 186, p. C5.

Examples of dibismuthine compounds are tetramethyldibismuthine, tetraethyldibismuthine, tetrapropyldibismuthine, tetraisopropyldibismuthine, tetrabutyldibismuthine, tetraisopropenyldibismuthine, tetraisobutenyldibismuthine, tetraphenyldibismuthine, tetrakis(trimethylsilyl)dibismuthine, 1,1,2,2-tetrakis(bis(trimethylsilyl)methyl)dibismuthine, 1,1'-bibismolane, etc.

In the case where a living radical polymer is prepared by admixing at least one compound selected from among a ditelluride compound, distibine compound and dibismuthine compound with a living radical polymerization initiator of the formula (2), or with a mixture of this initiator and an azo polymerization initiator as required, and polymerizing a vinyl monomer with use of the resulting mixture, this process can be practiced in the same manner the above-mentioned living radical polymer preparing process. Stated more specifically, the process is the same as the foregoing living radical polymer preparing process with the exception of admixing at least one compound selected from among a ditelluride compound, distibine compound and dibismuthine compound with a living radical polymerization initiator of the formula (2), or with a mixture of this initiator and an azo polymerization initiator as required, in a container in which the inside air is replaced with an inert gas.

The living radical polymerization initiator of the formula (2) and at least one compound selected from among a ditelluride compound, distibine compound and dibismuthine compound are used usually in such amounts that the compound selected from among a ditelluride compound, distibine compound and dibismuthine compound is used in an amount of 0.1 to 100 moles, preferably 0.1 to 10 moles, more preferably 0.1 to 5 moles, per mole of the living radical polymerization initiator of the formula (2).

The living radical polymerization initiator of the present invention is adapted for excellent control of molecular weights and molecular weight distributions under very mild conditions. In particular, in case of combined use of the present living radical polymerization initiator and the azo type polymerization initiator, the present polymerization reaction proceeds in a shortened reaction time than the conventional living radical polymerization reaction.

Different kinds of vinyl monomers are usable in the process of the invention for preparing a living radical polymer. For example when at least two kinds of vinyl monomers are reacted at the same time, a random copolymer can be obtained. The random copolymer obtained is a polymer which comprises the reacted monomers in the original ratio (mole ratio) regardless of the kinds of the monomers. When a random copolymer is obtained by reacting a vinyl monomer A and a vinyl monomer B at the same time, the copolymer has substantially the same material ratio (mole ratio). Further when two kinds of vinyl monomers are reacted in succession, a block copolymer can be obtained. The block copolymer is provided by the same order of reacted monomers regardless of the kinds of the monomers. When a vinyl monomer A and a vinyl monomer B are reacted to obtain a block copolymer, the polymer obtained is in the order of A-B or B-A in conformity with the order of monomers reacted.

The living radical polymer to be obtained by the invention is adjustable in molecular weight according to the reaction time and the amount of the organoantimony compound, and can be 500 to 1,000,000 in number average molecular weight. The invention is especially suitable for producing living radical polymers having a number average molecular weight of 1,000 to 50,000.

The living radical polymer to be obtained by the invention is controlled to 1.05 to 1.50 in molecular weight distribution (PD=Mw/Mn). The molecular weight distribution is controllable to a narrower range of 1.05 to 1.30, a further narrower range of 1.10 to 1.20, a still narrower range of 1.09 to 1.20, 1.09 to 1.17, 1.09 to 1.12.

It has been found that the living radical polymer of the present invention has a growth terminal which is highly reactive organostibanyl group. Accordingly, the organoantimony compound used for radical polymerization makes it easier to convert the terminal group to other functional group than in the case of the living radical polymer obtained by conventional living radical polymerization. Further, when at least one compound selected from among ditelluride compound, distibine compound and dibismuthine compound, a growth terminal is organotellanyl group, organostibanyl group or organobismuthanyl group.

The living radical polymer obtained according to the invention is therefore usable as a macro living radical polymerization initiator (macroinitiator).

A-B diblock copolymers such as methyl methacrylate-styrene and B-A diblock copolymers such as styrene-methyl methacrylate can be obtained using a macro living radical polymerization initiator of the invention. A-B-A triblock copolymers such as methyl methacrylate-styrene-methyl methacrylate and A-B-C triblock copolymers such as methyl methacrylate-styrene-butyl acrylate are also available. This is attributable to the fact that the vinyl monomers of various different types are controllable by the living radical polymerization initiator of the formula (2), and as required the azo type polymerization initiator, and also to the fact that highly reactive antimony is present at the growth terminal of the living radical polymer obtained with use of the living radical polymerization initiator.

Stated more specifically, block copolymers are prepared by the processes to be described below.

For preparing A-B diblock copolymers such as methyl methacrylate-styrene copolymer, methyl methacrylate, the living radical polymerization initiator of the formula (2), and as required the azo type polymerization initiator are mixed together first as in the process described above for preparing a living radical polymer to obtain poly(methyl methacrylate), and subsequently mixing styrene with the polymer to obtain methyl methacrylate-styrene copolymer.

A-B-A triblock copolymers and A-B-C triblock copolymers can be produced, for example, by preparing an A-B diblock copolymer by the above process and thereafter mixing a vinyl monomer (A) or vinyl monomer (C) with the copolymer to obtain the A-B-A or A-B-C triblock copolymer.

In producing the diblock copolymer according to the invention, the living radical polymerization initiator of the formula (2), and as required the azo type polymerization initiator and a ditelluride compound, etc. can be used when a homopolymer is prepared from the first monomer and/or when the diblock copolymer is subsequently prepared.

Further in producing the triblock copolymer according to the invention, the living radical polymerization initiator of the formula (2), and as required the azo type polymerization initiator and a ditelluride compound, etc. can be used at least once when a homopolymer is prepared from the first monomer, or when a diblock copolymer is subsequently prepared, or when the triblock copolymer is subsequently prepared.

The preparation of each block may be followed directly by the subsequent reaction for the next block, or the subsequent reaction for the next block may be initiated after the purification of the product resulting from the completion of the first reaction. The block copolymer can be isolated by a usual method. For example, the solvent used and the remaining monomer are removed in a vacuum to take out the desired polymer, or the desired product is isolated by re-precipitation using a solvent wherein the product is insoluble.

A resin containing an acid-dissociable group can be prepared by polymerizing a vinyl monomer using the living radical polymerization initiator of the invention and removing the growth terminal of the resulting living radical polymer. This resin is precision-controlled in molecular weight and molecular weight distribution (PD=Mw/Mn), is highly soluble in resist solvents and can be used suitably for resists for use in manufacturing semiconductor devices which are expected to be finer in structure.

In the case where the living radical polymerization initiator of the formula (2) is used, a metal atom remains at the growth terminal. It is desired that the amount of the remaining metal atom be up to 25 ppm based on the whole amount of the resin to ensure improvements in resist characteristics including the sensitivity and resolution of the resist and process stability.

After the polymer has been formed, the metal atom remaining at the terminal of the molecule is removed by a radical reduction method using tributylstannane or a thiol compound, an adsorption method using activated carbon, silica gel, activated alumina, activated clay, molecular sieves or high polymer adsorbent, a metal adsorption method using an ion exchange resin, a liquid-liquid extraction method for removing remaining metal compounds by the combination of water for washing and a suitable solvent, a solution purification method using ultrafiltration for extracting and removing substances having a molecular weight not greater than a specified value, or a combination of such methods.

Given below are examples of methods of purifying the resin of the invention containing an acid-dissociable group. Metals and like impurities are removed by adsorbing the metal from a resin solution using a zeta potential filter, or by washing a resin solution with an aqueous acid solution of oxalic acid or sulfonic acid to remove the metal as cherated. The remaining monomer or oligomer component is removed to a value not greater than a specified level by a liquid-liquid extraction method for removing the remaining monomer or oligomer component by the combination of water for washing and a suitable solvent, a solution purification method using ultrafiltration for extracting and removing substances having a molecular weight not greater than a specified value, a reprecipitation method for removing the remaining monomer or the like by dropwise adding a resin solution to a poor solvent to solidify the resin, and a solid purification method wherein a resin slurry filtered off is washed with a poor solvent. Such methods can be used in combination.

The poor solvent to be used in the reprecipitation method is dependent, for example, on the physical properties of the resin to be purified and can not be generally exemplified.

A suitable poor solvent is to be selected for use.

A radiation-sensitive resin composition can be obtained by using a radiation-sensitive acid producing agent, serving as a component for producing an acid when irradiated with radiation, in combination with the resin containing an acid-dissociable group.

The presence of the resin containing an acid-dissociable group in the radiation-sensitive resin composition renders the composition highly soluble in resist solvents, gives excellent basic properties to the resist and renders the composition extremely suitable for use in fabricating semiconductor devices which are expected to be made finer in structure.

Preferable examples of radiation-sensitive acid producing agents are triphenylsulfonium trifluoromethanesulfonate, triphenylsulfonium nonafluoro-n-butanesulfonate, triphenylsulfonium perfluoro-n-octanesulfonate, triphenylsulfonium-2-bicyclo[2.2.1]hept-2-yl-1,1,2,2-tetrafluoroethane-sulfonate, triphenylsulfonium-2-(3-tetracyclo[$4.4.0.1^{2,5}.1^{7,10}$]dodecanyl)-1,1-difluoroethanesulfonate, triphenylsulfonium N,N-bis(nonafluoro-n-butanesulfonyl)imidate, triphenylsulfonium camphorsulfonate, 4-cyclohexylphenyldiphenylsulfonium trifluoromethanesulfonate, 4-cyclohexylphenyldiphenyl-sulfonium nonafluoro-n-butanesulfonate, 4-cyclohexylphenyldiphenylsulfonium perfluoro-n-octanesulfonate, 4-cyclohexylphenyldiphenylsulfonium-2-bicyclo[2.2.1]hept-2-yl-1,1,2,2-tetrafluoroethanesulfonate, 4-cyclohexylphenyldiphenylsulfonium-2-(3-tetracyclo[$4.4.0.1^{2,5}.1^{7,10}$]dodecanyl)-1,1-difluoroethanesulfonate, 4-cyclohexylphenyldiphenylsulfonium N,N-bis(nonafluoro-n-butanesulfonyl)imidate, 4-cyclohexylphenyldiphenylsulfonium camphorsulfonate, 4-t-butylphenyldiphenylsulfonium trifluoromethanesulfonate, 4-t-butylphenyldiphenylsulfonium nonafluoro-n-butanesulfonate, 4-t-butylphenyldiphenylsulfonium perfluoro-n-octanesulfonate, 4-t-butylphenyldiphenylsulfonium-2-bicyclo[2.2.1]hept-2-yl-1,1,2,2-tetrafluoroethanesulfonate, 4-t-butylphenyldiphenylsulfonium-2-(3-tetracyclo[4.4.0.1$^{2,5}$.1$^{7,10}$]dodecanyl)-1,1-difluoroethanesulfonate, 4-t-butylphenyldiphenylsulfonium-N,N-bis(nonafluoro-n-butanesulfonyl)imidate, 4-t-butylphenyldiphenylsulfonium camphorsulfonate, tri(4-t-butylphenyl)sulfonium trifluoromethanesulfonate, tri(4-t-butylphenyl)sulfonium nonafluoro-n-butanesulfonate, tri(4-t-butylphenyl)sulfonium perfluoro-n-octanesulfonate, tri(4-t-butylphenyl)sulfonium-2-bicyclo[2.2.1]hept-2-yl-1,1,2,2-tetrafluoroethanesulfonate, tri(4-t-butylphenyl)sulfonium 2-(3-tetracyclo[4.4.0.1$^{2,5}$.1$^{7.10}$]dodecanyl)-1,1-difluoroethanesulfonate, tri(4-t-butylphenyl)sulfonium N,N-bis(nonafluoro-n-butanesulfonyl)imidate, tri(4-t-butylphenyl)sulfonium camphorsulfonate, diphenyliodonium trifluoromethanesulfonate, diphenyliodonium nonafluoro-n-butanesulfonate, diphenyliodonium perfluoro-n-octanesulfonate, diphenyliodonium-2-bicylco[2.2.1]hept-2-yl-1,1,2,2-tetrafluoroethanesulfonate, diphenyliodonium-2-(3-tetracyclo[4.4.0.1$^{2,5}$.1$^{7,10}$]dodecanyl)-1,1-difluoroethanesulfonate, diphenyliodonium N,N-bis(nonafluoro-n-butanesulfonyl) imidate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium-2-bicyclo[2.2.1]hept-2-yl-1,1,2,2-tetrafluoroethanesulfonate, bis(4-t-butylphenyl)iodonium-2-(3-tetracyclo[4.4.0.1$^{2,5}$.1$^{7,10}$]dodecanyl)-1,1-difluoroethanesulfonate, bis(4-t-butylphenyl)iodonium-N,N-bis(nonafluoro-n-butanesulfonyl)imidate, bis(4-t-butylphenyl)iodonium camphorsulfonate, 1-(4-n-butoxynaphthalene-1-yl)tetrahydrothiophenium trifluoromethanesulfonate, 1-(4-n-butoxynaphthalene-1-yl)tetrahydrothiophenium nonafluoro-n-butanesulfonate, 1-(4-n-butoxynaphthalene-1-yl)tetrahydrothiophenium perfluoro-n-octanesulfonate, 1-(4-n-butoxynaphthalene-1-yl)tetrahydrothiophenium-2-bicyclo[2.2.1]hept-2-yl-1,1,2,2-tetrafluoroethanesulfonate, 1-(4-n-butoxynaphthalene-1-yl)tetrahydrothiophenium 2-(3-tetracyclo[4.4.0.1$^{2,5}$.1$^{7,10}$]dodecanyl)-1,1-difluoroethanesulfonate, 1-(4-n-butoxynaphthalene-1-yl)tetrahydrothiophenium-N,N-bis(nonafluoro-n-butanesulfonyl)imidate, 1-(4-n-butoxynaphthalene-1-yl)tetrahydrothiophenium champhersulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium-2-bicyclo[2.2.1]hept-2-yl-1,1,2,2-tetrafluoroethanesulfonate, 1-(3,5-dimethyl-4-hydroxyphenyl)tetrahydrothiophenium-2-(3-tetracyclo[4.4.0.1$^{2,5}$.1$^{7,10}$]dodecanyl)-1,1-difluoroethanesulfonate, 1-(3,5-dimethyl-4-hydroxyphenyl)tetrahydrothiophenium-N,N-bis(nonafluoro-n-butanesulfonyl)imidate, 1-(3,5-dimethyl-4-hydroxyphenyl)tetrahydrothiophenium camphorsulfonate, N-(trifluoromethanesulfonyloxy)succinimide, N-(nonafluoro-n-butanesulfonyloxy)succinimide, N-(perfluoro-n-octanesulfonyloxy)succinimide, N-(2-bicyclo[2.2.1]hept-2-yl-1,1,2,2-tetrafluoroethanesulfonyloxy)succinimide, N-(2-(3-tetracyclo[4.4.0.1$^{2,5}$.1$^{7,10}$]dodecanyl)-1,1-difluoroethanesulfonyloxy)succinimide, N-(camphorsulfonyloxy)succinimide, N-(trifluoromethanesulfonyloxy)bicyclo[2.2.1]hept-5-en-2,3-dicarboxylmide, N-(nonafluoro-n-butanesulfonyloxy)bicyclo[2.2.1]hept-5-en-2,3-dicarboxylmide, N-(perfluoro-n-octanesulfonyloxy)bicyclo[2.2.1]hept-5-en-2,3-dicarboxylmide, N-(2-bicyclo[2.2.1]hept-2-yl-1,1,2,2-tetrafluoroethanesulfonyloxy)bicyclo[2.2.1]hept-5-en-2,3-dicarboxylmide, N-(2-(3-tetracyclo[4.4.0.1$^{2,5}$.1$^{7,10}$]dodecanyl)-1,1-difluoroethanesulfonyloxy)bicyclo[2.2.1]hept-5-en-2,3-dicarboxylmide, N-(camphorsulfonyloxy)bicyclo[2.2.1]hept-5-en-2,3-dicarboxylmide, etc.

According to the invention, radiation-sensitive acid producing agents can be used singly, or at least two of them are usable in admixture.

To ensure the sensitivity of the resist and the amenability thereof to development, the radiation-sensitive acid producing agent is used usually in an amount of 0.1 to 20 parts by weight, preferably 0.1 to 7 parts by weight, per 100 parts by weight of the resin containing an acid-dissociable group. If the amount of acid producing agent is less than 0.1 part by weight, lower sensitivity and impaired developability tend to result, whereas if the amount is in excess of 20 parts by weight, lower transparency to radiation will result, making is less likely to obtain rectangular resist patterns.

BEST MODE OF CARRYING OUT THE INVENTION

The present invention will be described below in detail with reference to Reference Examples, Examples and Test Examples, but is not limited thereto in any way.

The present invention will be described below in detail with reference to Examples, but is not limited thereto in any way. In Examples and Comparative Examples, properties were determined by the following methods.

Identification of organantimony compounds and living radical polymers

The organoantimony compound was identified based on the results of $^1$H-NMR and MS analyses. The molecular weight and molecular weight distribution of the living radical polymer were determined using GPC (gel permeation chromatography). The measuring instruments used are as follows.

$^1$H-NMR: Varian Gemini 2000 (300 MHz for $^1$H), JEOL JNM-A400 (400 MHz for $^1$H)

$^{13}$C-NMR: Varian Gemini 2000, JEOL JNM-A400

MS (HRMS): JEOL JMS-300

Molecular weight and molecular weight distribution: liquid chromatography Shimadzu LC-10 [column: Shodex K-804L+K-805L, polystyrene standard: TOSOH TSK Standard, poly(methyl methacrylate) standard: Shodex Standard M-75]

The adamantane monomer MADM and norbornene monomer NBLM used in Example 85 and Example 86 have the following structural formulae.

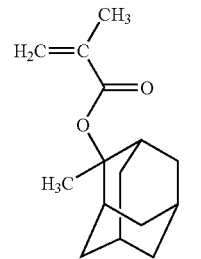

Adamantane monomer MADM

-continued

Norbornene monomer NBLM

Preparation Example 1

Preparation of Trimethylstibanyl Dibromide

A methylmagnesium iodide solution was prepared by placing 37.7 g (1.55 moles) of magnesium and 235.4 g (1.65 moles) of methyl iodide into 900 ml of diethyl ether. A solution of 114 g (0.5 mole) of antimony trichloride in 100 ml of THF was slowly added dropwise to the iodide solution at 0° C. (over a period of 40 minutes). The mixture was thereafter stirred at room temperature for 1.5 hours. A salt formed as a by-product was filtered off, and the solvent was concentrated and distilled in a vacuum (20-30° C., 200-300 mmHg). Bromine was added to the resulting liquid with stirring (until the liquid became colored owing to the addition of bromine). The precipitate obtained was washed several times with cold ether and then dried in a vacuum at room temperature, affording 115.6 g of a white solid (71% in yield). $^1$H-NMR and $^{13}$C-NMR revealed that the product was the desired one.

IR (KBr) 3007, 1792, 1720, 1394, 874, 669, 569
$^1$H-NMR (400 MHz, CDCl$_3$) 2.64 (s, 9H)
$^{13}$C-NMR (100 MHz, CDCl$_3$); 26.57

Preparation Example 2

Preparation of Dimethylstibanyl Bromide

Trimethylstibanyl dibromide (16.3 g, 50 mmole) was heated at 180° C. in a vacuum (50 mmHg), and thereafter distilled, giving 9.27 g of dimethylstibanyl bromide (90.0% in yield).

IR (neat) 2995, 2912, 1400, 1202, 1020, 843, 768, 517
$^1$H-NMR (400 MHz, CDCl$_3$) 1.58 (s, 6H)
$^{13}$C-NMR (100 MHz, CDCl$_3$) 8.61
HRMS (EI) m/z: Calcd for C$_2$H$_6$BrSb (M)$^+$, 229.8691; Found 229.8663.

Preparation Example 3

Dimethyl Ditelluride

A 3.19 g quantity (25 mmole) of metallic tellurium [product of Aldrich, brand name: Tellurium (−40 mesh)] was suspended in 25 ml of THF, and 25 ml (28.5 mmole) of methyllithium [product of Kanto Chemical Co, Ltd., diethyl ether solution] was added slowly to the suspension at 0° C. (10 minutes). The reaction mixture was stirred until the metallic tellurium disappeared completely (10 minutes). To the resulting reaction mixture was added 20 ml of a solution of ammonium chloride at room temperature, followed by stirring for 1 hour. The organic layer was separated off, and the aqueous layer was subjected to extraction with diethyl ether 3 times. The organic layers were collected, dried over anhydrous sodium sulfate and concentrated in a vacuum, affording 2.69 g (9.4 mmole, yield 75%) of blackish purple oil.

The product was found to be dimethyl ditelluride by MS (HRMS) and $^1$H-NMR.

HRMS (EI) m/z: Calcd for C$_2$H$_6$Te$_2$(M)$^+$, 289.8594; Found 289.8593
$^1$H-NMR (300 MHz, CDCl$_3$) 2.67 (s, 6H)

Preparation Example 4

Tetramethyldistibine

A 465 mg quantity (19.4 mmole) of magnesium (flaky) was suspended in 25 ml of THF, and a THF solution of 4.42 g (19.0 mmole) of the dimethylstibanyl bromide prepared in Preparation Example 2 was slowly added to the suspension at room temperature. The reaction mixture was thereafter stirred at 70° C. for 1 hour, the solvent was concentrated in a vacuum, 20 ml of hexane was added to an oily product obtained, and the resulting solution was collected. The collected solution was concentrated in a vacuum and subsequently distilled in a vacuum (room temperature, 0.1 mmHg) to obtain 0.30 g of an oily product (1.9 mmole, 10% in yield). $^1$H-NMR indicated that the product was tetramethyldistibine.

$^1$H-NMR (400 MHz, CDCl$_3$) 0.98 (s)

Example 1

Preparation of ethyl 2-dimethylstibanyl-2-methylpropionate

A 3.48 g quantity (30 mmole) of ethyl isobutyrate was added to 50 ml of THF, and the mixture was chilled to −78° C. To the mixture was slowly added 16.5 ml (33 mmole) of lithium isopropylamide (product of Aldrich, 2.0M heptane-THF-ethylbenzene solution) over a period of 10 minutes. The reaction mixture was stirred while being held at −78° C. (for 1 hour). To the resulting solution was added 6.9 g (29.8 mmole) of dimethylstibanyl bromide at 0° C., followed by stirring at room temperature for 2 hours. After the completion of the reaction, the solvent was concentrated in a vacuum and subsequently distilled in a vacuum, giving 3.98 g of a colorless oily product (50.0% in yield), b.p. 53-55° C./1.6-1.8 mmHg. MS (HRMS), $^1$H-NMR and $^{13}$C-NMR revealed that the product was the desired one.

IR (neat) 2980, 2909, 2864, 1697, 1468, 1384, 1252, 1136, 1032, 770, 515
$^1$H-NMR (400 MHz, CDCl$_3$) 0.76 (s, 6H, SbMe$_2$), 1.26 (t, J=7.2 Hz, 3H) 1.43 (s, 6H), 4.11 (q, J=7.2 Hz, 2H)
$^{13}$C-NMR (100 MHz, CDCl$_3$) −1.51, 14.89, 23.59, 31.56, 59.84, 176.67
HRMS(CI) m/z: Calcd for C$_8$H$_{18}$O$_2$Sb (M+H)$^+$, 267.0345; Found 267.0362

Example 2

Preparation of 2-methyl-2-dimethylstibanyl-propionitrile

A 2.07 g (30 mmole) of isobutyronitrile was added to 50 ml of THF, and the mixture was chilled to −78° C. To the mixture was slowly added 16.5 ml (33 mmole) of lithium isopropylamide (product of Aldrich, 2.0M heptane-THF, ethylbenzene solution) over a period of 15 minutes. The reaction mixture was stirred while being held at −78° C. (for 1 hour). To the resulting solution was added 6.9 g (29.8 mmole) of dimethylstibanyl bromide at 0° C., followed by stirring at room temperature for 2 hours. After the completion of the reaction, the solvent was concentrated in a vacuum and subsequently distilled in a vacuum, giving 2.3 g of a colorless oily product (35.0% in yield), b.p. 55-57° C./3 mmHg.

MS (HRMS) and $^1$H-NMR revealed that the product was the desired one.

IR(Nujol) 2860, 2206, 1713, 1452, 1371, 1211, 1121, 1016, 933, 775, 721, 665, 517

$^1$H-NMR (400 MHz, CDCl$_3$) 0.95 (s, 6H, SbMe$_2$), 1.50 (s, 6H)

$^{13}$C-NMR (100 MHz, CDCl$_3$) −0.43, 14.51, 25.22, 126.11

HRMS (EI) m/z: Calcd for C$_6$H$_{12}$NSb (M)$^+$, 219.0008; Found 219.0028.

Example 3

Preparation of 1-dimethylstibanyl-ethyl)benzene

A 9.8 g quantity (30 mmole) of trimethylstibanyl bromide was suspended in 100 ml of liquid ammonia, the suspension was chilled to −78° C., and 2.87 g (125 mmole) of metal sodium was slowly added to the suspension (over a period of 10 minutes). The reaction mixture was stirred (for 1 hour) while being held at −78° C., and 2.94 g (30 mmole) of ammonium bromide was subsequently slowly added to the mixture. The resulting mixture was stirred for 1 hour, the solvent was then distilled off, and 100 ml of THF was thereafter added to the residue. To the mixture was added 6.11 g (33 mmole) of (1-bromoethyl)benzene, followed by stirring at 0° C. for 4 hours. After the completion of the reaction, the solvent was concentrated in a vacuum, and the resulting mixture was distilled in a vacuum, giving 3.28 g of a colorless oily product (43% in yield), b.p. 53-57° C./1.3 mmHg. MS (HRMS), $^1$H-NMR and $^{12}$C-NMR indicated that the product was the desired one.

IR (neat) 2980, 2903, 2864, 1599, 1491, 1450, 1375, 1202, 1013, 764, 698, 665, 515

$^1$H-NMR (400 MHz, CDCl$_3$) 0.53 and 0.63 (s, 6H, SbMe$_2$), 1.60 (d, J=7.2 Hz, 3H), 2.99 (q, J=7.2 Hz, 1H), 7.02-7.06 (m, 3H)

$^{13}$C-NMR (100 MHz, CDCl$_3$) −2.62, −2.09, 18.79, 29.78, 124.78, 126.45, 128.35, 146.51

HRMS (EI) m/z: Calcd for C$_{10}$H$_{15}$Sb (M)$^+$, 256.0212; Found 256.0207

Example 4

Along with 1.04 g (10 mmole) of styrene, 26.7 mg (0.10 mmole) of ethyl 2-dimethylstibanyl-2-methyl propionate prepared in Example 1 was placed into a glove box with the inside air replaced by nitrogen, followed by stirring at 100° C. for 48 hours. After the completion of the reaction, the reaction mixture was dissolved in 5 ml of chloroform, and the solution was then poured into 250 ml of methanol which was being stirred. The resulting polymer precipitate was collected by suction filtration and dried to obtain polystyrene (yield 82%).

GPC analysis (with reference to the molecular weight of an authentic sample of polystyrene) revealed Mn=7700 and PD=1.14.

Examples 5 to 9

Along with styrene, 26.7 mg (0.10 mmole) of ethyl 2-dimethylstibanyl-2-methyl propionate prepared in Example 1 and 8.21 mg (0.05 mmole) of 2,2'-azobis(isobutyronitrile) [Otsuka Chemical Co, Ltd., AIBN, hereinafter same] were placed into a glove box with the inside air replaced by nitrogen, and the reactions were carried out as shown in Table 1. After the completion of the reaction, the reaction mixture was dissolved in 5 ml of chloroform, and the solution was then poured into 250 ml of methanol which was being stirred. The resulting polymer precipitate was collected by suction filtration and dried to obtain polystyrene GPC analysis (with reference to the molecular weight of an authentic sample of polystyrene) was given in Table 1.

TABLE 1

|  | styrene (mmol) | reaction condition (° C./h) | yield (%) | Mn | PD |
| --- | --- | --- | --- | --- | --- |
| Ex. 5 | 10 | 60/19 | 99 | 8700 | 1.17 |
| Ex. 6 | 20 | 60/24 | 99 | 15800 | 1.22 |
| Ex. 7 | 50 | 60/36 | 80 | 24800 | 1.15 |
| Ex. 8 | 70 | 60/36 | 76 | 41200 | 1.16 |
| Ex. 9 | 100 | 60/36 | 65 | 49400 | 1.23 |

Example 10

Along with 1.04 g (10 mmole) of styrene, 22.0 mg (0.10 mmole) of 2-methyl-2-dimethylstibanyl-propionitrile prepared in Example 2 and 8.21 mg (0.05 mmole) of 2,2'-azobis(isobutyronitrile) were placed into a glove box with the inside air replaced by nitrogen, followed by stirring at 60° C. for 14 hours. After the completion of the reaction, the reaction mixture was dissolved in 5 ml of chloroform, and the solution was then poured into 200 ml of methanol which was being stirred. The resulting polymer precipitate was collected by suction filtration and dried to obtain polystyrene (yield 95%).

GPC analysis (with reference to the molecular weight of an authentic sample of polystyrene) revealed Mn=9000 and PD=1.17.

Example 11

Along with 1.04 g (10 mmole) of styrene, 25.7 mg (0.10 mmole) of (1-dimethylstibanyl-ethyl)benzene prepared in Example 3 and 16.42 mg (0.10 mmole) of 2,2'-azobis(isobutyronitrile) were placed into a glove box with the inside air replaced by nitrogen, followed by stirring at 60° C. for 13 hours. After the completion of the reaction, the reaction mixture was dissolved in 5 ml of chloroform, and the solution was then poured into 200 ml of methanol which was being stirred. The resulting polymer precipitate was collected by suction filtration and dried to obtain polystyrene (yield 99%).

GPC analysis (with reference to the molecular weight of an authentic sample of polystyrene) revealed Mn=9300 and PD=1.22.

Example 12

Along with 1.28 g (10 mmole) of n-butyl acrylate [stabilized with hydroquinone methyl ether (MEHQ)], 26.7 mg (0.10 mmole) of ethyl 2-dimethylstibanyl-2-methyl propionate prepared in Example 1 and 4.93 mg (0.03 mmole) of 2,2'-azobis(isobutyronitrile) were placed into a glove box with the inside air replaced by nitrogen, followed by stirring at 60° C. for 1 hour. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(n-butyl acrylate) (yield 96%).

GPC analysis [with reference to the molecular weight of an authentic sample of poly(methyl methacrylate)] revealed Mn=12400 and PD=1.13.

Example 13

Along with 1.00 g (10 mmole) of methyl methacrylate [stabilized with hydroquinone (HQ)], 26.7 mg (0.10 mmole) of ethyl 2-dimethylstibanyl-2-methyl propionate prepared in Example 1 and 4.93 mg (0.03 mmole) of 2,2'-azobis(isobutyronitrile) were placed into a glove box with the inside air replaced by nitrogen, followed by stirring at 60° C. for 4 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(methyl methacrylate) (yield 100%).

GPC analysis [with reference to the molecular weight of an authentic sample of poly(methyl methacrylate)] revealed Mn=11000 and PD=1.24.

Example 14

Along with 1.00 g (10 mmole) of methyl methacrylate (stabilized with HQ), 22.0 mg (0.10 mmole) of 2-methyl-2-dimethylstibanyl propionitrile prepared in Example 2 and 16.42 mg (0.10 mmole) of 2,2'-azobis(isobutyronitrile) were placed into a glove box with the inside air replaced by nitrogen, followed by stirring at 60° C. for 4 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(methyl methacrylate) (yield 99%).

GPC analysis [with reference to the molecular weight of an authentic sample of poly(methyl methacrylate)] revealed Mn=12700 and PD=1.25.

Example 15

Along with 1.00 g (10 mmole) of methyl methacrylate (stabilized with HQ), 25.7 mg (0.10 mmole) of (1-dimethylstibanyl-ethyl)benzene prepared in Example 3 and 8.21 mg (0.05 mmole) of 2,2'-azobis(isobutyronitrile) were placed into a glove box with the inside air replaced by nitrogen, followed by stirring at 60° C. for 4 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(methyl methacrylate) (yield 92%).

GPC analysis [with reference to the molecular weight of an authentic sample of poly(methyl methacrylate)] revealed Mn=10700 and PD=1.21.

Example 16

Along with 1.13 g (10 mmole) of N-isopropylacrylamide (Wako Pure Chemical Industries, Ltd.), 26.7 mg (0.10 mmole) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 12 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(N-isopropylacrylamide) (yield 99%).

GPC analysis [with reference to the molecular weight of an authentic sample of poly(methyl methacrylate)] revealed Mn=15600 and PD=1.07.

Example 17

Along with 3.39 g (50 mmole) of N-isopropylacrylamide (same as above), 26.7 mg (0.10 mmole) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 12 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(N-isopropylacrylamide) (yield 99%).

GPC analysis [with reference to the molecular weight of an authentic sample of poly(methyl methacrylate)] revealed Mn=34200 and PD=1.20.

Example 18

Along with 0.53 g (10 mmole) of acrylonitrile (Wako Pure Chemical Industries, Ltd.), 26.7 mg (0.10 mmole) of ethyl 2-dimethylstibanyl-2-methylpropionate prepared in Example 1 and 8.21 mg (0.05 mmole) of 2,2'-azobis(isobutyronitrile) and 1.35 ml of N,N-dimethylformamide (DMF) were placed into a glove box with the inside air replaced by nitrogen, followed by stirring at 60° C. for 6 hours. After the completion of the reaction, solvent and the remained monomer were removed under reduced pressure by vacuum pump to obtain polyacrylonitrile (yield 98%).

GPC analysis [with reference to the molecular weight of an authentic sample of poly(methyl methacrylate)] revealed Mn=17600 and PD=1.14.

Example 19

Along with 1.11 g (10 mmole) of 1-vinyl-2-pyrrolidone (Wako Pure Chemical Industries, Ltd.), 26.7 mg (0.10 mmole) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 0.5 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(1-vinyl-pyrrolidone) (yield 99%).

GPC analysis [with reference to the molecular weight of an authentic sample of poly(methyl methacrylate)] revealed Mn=10800 and PD=1.14.

Example 20

Along with 3.33 g (30 mmole) of 1-vinyl-2-pyrrolidone (Wako Pure Chemical Industries, Ltd.), 26.7 mg (0.10 mmole) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 7 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(1-vinyl-pyrrolidone) (yield 99%).

GPC analysis [with reference to the molecular weight of an authentic sample of poly(methyl methacrylate)] revealed $Mn=30600$ and $PD=1.21$.

Example 21

Along with 5.55 g (50 mmole) of 1-vinyl-2-pyrrolidone (Wako Pure Chemical Industries, Ltd.), 26.7 mg (0.10 mmole) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 1 hour. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(1-vinyl-pyrrolidone) (yield 99%).

GPC analysis [with reference to the molecular weight of an authentic sample of poly(methyl methacrylate)] revealed $Mn=38100$ and $PD=1.26$.

Example 22

Along with 0.22 g (2.5 mmole) of vinyl acetate (Wako Pure Chemical Industries, Ltd.), 26.7 mg (0.10 mmole) of ethyl 2-dimethylstibanyl-2-methylpropionate prepared in Example 1 and 2.00 mg (0.0125 mmole) of 2,2'-azobis(isobutyronitrile) were placed into a glove box with the inside air replaced by nitrogen, followed by stirring at 60° C. for 5 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(vinyl acetate) (yield 92%).

GPC analysis [with reference to the molecular weight of an authentic sample of poly(methyl methacrylate)] revealed $Mn=2800$ and $PD=1.26$.

Example 23

Along with 0.686 g (6.6 mmole) of styrene, 0.33 mg (3.3 mmole) of methyl methacrylate (same as above), 26.7 mg (0.10 mmol) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 15 hours. After the completion of the reaction, the reaction mixture was dissolved in 3 ml of chloroform, and the solution was then poured into 200 ml of hexane which was being stirred. The resulting polymer precipitate was collected by suction filtration and dried to obtain a random copolymer of poly(styrene-r-methyl methacrylate) (0.94 g, yield 92.5%).

GPC analysis [with reference to the molecular weight of an authentic sample of polystyrene] revealed $Mn=12000$ and $PD=1.18$.

Example 24

Along with 0.52 g (5.0 mmole) of styrene, 0.50 g (5.0 mmole) of methyl methacrylate (same as above), 26.7 mg (0.10 mmol) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 15 hours. After the completion of the reaction, the reaction mixture was dissolved in 3 ml of chloroform, and the solution was then poured into 200 ml of hexane which was being stirred. The resulting polymer precipitate was collected by suction filtration and dried to obtain a random copolymer of poly(styrene-r-methyl methacrylate) (0.92 g, yield 90.2%).

GPC analysis [with reference to the molecular weight of an authentic sample of polystyrene] revealed $Mn=13500$ and $PD=1.16$.

Example 25

Along with 0.343 g (3.3 mmole) of styrene, 0.66 g (6.6 mmole) of methyl methacrylate (same as above), 26.7 mg (0.10 mmol) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 15 hours. After the completion of the reaction, the reaction mixture was dissolved in 3 ml of chloroform, and the solution was then poured into 200 ml of hexane which was being stirred. The resulting polymer precipitate was collected by suction filtration and dried to obtain a random copolymer of poly(styrene-r-methyl methacrylate) (0.91 g, yield 91.0%).

GPC analysis [with reference to the molecular weight of an authentic sample of polystyrene] revealed $Mn=12800$ and $PD=1.17$.

Example 26

Along with 0.50 g (5.0 mmole) of methyl methacrylate (same as above), 0.555 g (5.0 mmole) of 1-vinyl-2-pyrrolidone, 26.7 mg (0.10 mmol) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 27 hours. After the completion of the reaction, the reaction mixture was dissolved in 3 ml of chloroform, and the solution was then poured into 200 ml of hexane which was being stirred. The resulting polymer precipitate was collected by suction filtration and dried to obtain a random copolymer of poly(methyl methacrylate-r-1-vinyl-2-pyrrolidone) (0.88 g, yield 81.9%).

GPC analysis [with reference to the molecular weight of an authentic sample of poly(methyl methacrylate)] revealed $Mn=15200$ and $PD=1.23$.

Example 27

Along with 0.52 g (5.0 mmole) of styrene, 0.555 g (5.0 mmole) of 1-vinyl-2-pyrrolidone, 26.7 mg (0.10 mmol) of ethyl 2-dimethylstibanyl-2-methylpropionate prepared in Example 1 and 8.21 mg (0.05 mmole) of 2,2'-azobis(isobutyronitrile) were placed into a glove box with the inside air replaced by nitrogen, followed by stirring at 60° C. for 15 hours. After the completion of the reaction, the reaction mixture was dissolved in 3 ml of chloroform, and the solution was then poured into 200 ml of hexane which was being stirred. The resulting polymer precipitate was collected by suction filtration and dried to obtain a random copolymer of poly(styrene-r-1-vinyl-2-pyrrolidone) (0.93 g, yield 88.2%).

Example 28

Along with 1.04 g (10 mmole) of styrene and 53.4 mg (0.20 mmole) of ethyl 2-dimethylstibanyl-2-methylpropionate prepared in Example 1 were placed into a glove box with the inside air replaced by nitrogen, followed by stirring at 110° C. for 24 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain polystyrene macroinitiator.

GPC analysis [with reference to the molecular weight of an authentic sample of polystyrene] revealed Mn=4400 and PD=1.05.

Example 29

Along with 0.64 g (5.7 mmole) of 1-vinyl-2-pyrrolidone, 0.23 g (0.05 mmol) of polystyrene macroinitiator prepared in Example 28, 2.3 mg (0.014 mmole) of 2,2'-azobis(isobutyronitrile) and 1 ml of N,N-dimethylformamide (DMF) were placed into a glove box with the inside air replaced by nitrogen, followed by stirring at 60° C. for 8 hours. After the completion of the reaction, the reaction mixture was dissolved in 5 ml of chloroform, and the solution was then poured into 300 ml of diethyl ether which was being stirred. The resulting polymer precipitate was collected by suction filtration and dried to obtain block copolymer of poly(styrene-b-1-vinyl-2-pyrrolidone).

GPC analysis [with reference to the molecular weight of an authentic sample of polystyrene] revealed Mn=27100 and PD=1.05.

Example 30

Along with 2.00 g (20 mmole) of methyl methacrylate (same as above) and 106.8 mg (0.40 mmole) of ethyl 2-dimethylstibanyl-2-methylpropionate prepared in Example 1 were placed into a glove box with the inside air replaced by nitrogen, followed by stirring at 100° C. for 48 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain of poly(methyl methacrylate) macroinitiator.

GPC analysis [with reference to the molecular weight of an authentic sample of poly(methyl methacrylate)] revealed Mn=4700 and PD=1.27.

Example 31

Along with 0.50 g (4.4 mmole) of 1-vinyl-2-pyrrolidone, 0.19 g (0.04 mmol) of poly(methyl methacrylate) macroinitiator prepared in Example 30, 1.8 mg (0.011 mmole) of 2,2'-azobis(isobutyronitrile) and 1 ml of N,N-dimethylformamide (DMF) were placed into a glove box with the inside air replaced by nitrogen, followed by stirring at 60° C. for 8 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain block copolymer of poly(methyl methacrylate-b-1-vinyl-2-pyrrolidone).

GPC analysis [with reference to the molecular weight of an authentic sample of poly(methyl methacrylate)] revealed Mn=20500 and PD=1.30.

Example 32

Along with 1.00 g (10 mmole) of methyl methacrylate (same as above) and 26.7 mg (0.10 mmole) of ethyl 2-dimethylstibanyl-2-methylpropionate prepared in Example 1 were placed into a glove box with the inside air replaced by nitrogen, followed by stirring at 100° C. for 48 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 77%).

GPC analysis [with reference to the molecular weight of an authentic sample of poly(methyl methacrylate)] revealed Mn=8800 and PD=1.31.

Example 33

Along with 1.00 g (10 mmole) of methyl methacrylate (same as above), 26.7 mg (0.10 mmole) of ethyl 2-dimethylstibanyl-2-methylpropionate prepared in Example 1 and 3.29 mg (0.02 mmol) 2,2'-azobis(isobutyronitrile) were placed into a glove box with the inside air replaced by nitrogen, followed by stirring at 60° C. for 4 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 99%).

GPC analysis [with reference to the molecular weight of an authentic sample of poly(methyl methacrylate)] revealed Mn=9000 and PD=1.23.

Example 34

Along with 1.00 g (10 mmole) of methyl methacrylate (same as above), 26.7 mg (0.10 mmole) of ethyl 2-dimethylstibanyl-2-methylpropionate prepared in Example 1 and 8.2 mg (0.05 mmol) 2,2'-azobis(isobutyronitrile) were placed into a glove box with the inside air replaced by nitrogen, followed by stirring at 60° C. for 3.5 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 92%).

GPC analysis [with reference to the molecular weight of an authentic sample of poly(methyl methacrylate)] revealed Mn=10000 and PD=1.30.

Example 35

Along with 1.00 g (10 mmole) of methyl methacrylate (same as above), 26.7 mg (0.10 mmole) of ethyl 2-dimethylstibanyl-2-methylpropionate prepared in Example 1 and 16.42 mg (0.10 mmol) 2,2'-azobis(isobutyronitrile) were placed into a glove box with the inside air replaced by nitrogen, followed by stirring at 60° C. for 3.5 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 94%).

GPC analysis [with reference to the molecular weight of an authentic sample of poly(methyl methacrylate)] revealed Mn=9600 and PD=1.32.

Example 36

Along with 2.00 g (20 mmole) of methyl methacrylate (same as above), 53.4 mg (0.20 mmole) of ethyl 2-dimethylstibanyl-2-methylpropionate prepared in Example 1, 16.4 mg (0.10 mmol) of 2,2'-azobis(isobutyronitrile) and 2 g of toluene (Wako Pure Chemical Industries, Ltd.), were placed into a glove box with the inside air replaced by nitrogen, followed by stirring at 60° C. for 20 hours. After the completion of the reaction, the reaction mixture was dissolved in 4 ml of tetrahydrofuran, and the solution was then poured into 250 ml of methanol which was being stirred. The resulting polymer precipitate was collected by suction filtration and dried to obtain of poly(methyl methacrylate) (yield 100%).

GPC analysis [with reference to the molecular weight of an authentic sample of poly(methyl methacrylate)] revealed Mn=12,700 and PD=1.24.

Example 37

In a glove box having its inside air replaced by nitrogen, a liquid mixture was prepared from 1.00 g (10 mmole) of methyl methacrylate (the same as above), 26.7 mg (0.10 mmole) of the ethyl 2-dimethylstibanyl-2-methylpropionate prepared in Example 1, 8.2 mg (0.05 mmole) of 2,2'-azobis (isobutyronitrile), 9 mg of POVAL (product of Nippon Synthetic Chemical Industry Co., Ltd., 88% in saponification degree, brand name GH-17) and 3 g of distilled water fully deaerated by nitrogen bubbling. The mixture was irradiated with ultrasonic waves for 120 seconds to obtain a uniform dispersion. The dispersion was stirred at 60° C. for 20 hours. After the completion of the reaction, the reaction mixture was dissolved in 10 ml of chloroform, and the solution was placed into 300 ml of methanol with stirring. The resulting polymer precipitate was treated by suction filtration and dried, affording 94% of polymethyl methacrylate (94% in yield).

GPC analysis [with reference to the molecular weight of an authentic sample of poly(methyl methacrylate)] revealed Mn=9,700 and PD=1.29.

Example 38

Along with 1.00 g (10 mmole) of methyl methacrylate (same as above), 26.7 mg (0.10 mmole) of ethyl 2-dimethylstibanyl-2-methylpropionate prepared in Example 1, 30.3 mg (0.10 mmol) of tetramethyldistibine prepared in Preparation Example 4 and 3.29 mg (0.02 mmol) of 2,2'-azobis(isobutyronitrile) were placed into a glove box with the inside air replaced by nitrogen, followed by stirring at 60° C. for 14 hours. After the completion of the reaction, the reaction mixture was dissolved in 3 ml of chloroform, and the solution was then poured into 200 ml of methanol which was being stirred. The resulting polymer precipitate was collected by suction filtration and dried to obtain of poly(methyl methacrylate) (yield 85%).

GPC analysis [with reference to the molecular weight of an authentic sample of poly(methyl methacrylate)] revealed Mn=8,100 and PD=1.07.

Example 39

Along with 2.00 g (20 mmole) of methyl methacrylate (same as above), 53.4 mg (0.20 mmole) of ethyl 2-dimethylstibanyl-2-methylpropionate prepared in Example 1, 28.5 mg (0.10 mmol) of dimethyl ditelluride prepared in Preparation Example 3 and 2 g of toluene (Wako Pure Chemical Industries, Ltd.), were placed into a glove box with the inside air replaced by nitrogen, followed by stirring at 90° C. for 48 hours. After the completion of the reaction, the reaction mixture was dissolved in 4 ml of tetrahydrofuran, and the solution was then poured into 300 ml of methanol which was being stirred. The resulting polymer precipitate was collected by suction filtration and dried to obtain of poly(methyl methacrylate) (yield 95%).

GPC analysis [with reference to the molecular weight of an authentic sample of poly(methyl methacrylate)] revealed Mn=10,600 and PD=1.08.

Example 40

Along with 2.00 g (20 mmole) of methyl methacrylate (same as above), 53.4 mg (0.20 mmole) of ethyl 2-dimethylstibanyl-2-methylpropionate prepared in Example 1, 16.4 mg (0.10 mmol) of 2,2'-azobis(isobutyronitrile), 28.5 mg (0.10 mmol) of dimethyl ditelluride prepared in Preparation Example 3 and 2 g of toluene (Wako Pure Chemical Industries, Ltd.), were placed into a glove box with the inside air replaced by nitrogen, followed by stirring at 60° C. for 20 hours. After the completion of the reaction, the reaction mixture was dissolved in 4 ml of tetrahydrofuran, and the solution was then poured into 300 ml of methanol which was being stirred. The resulting polymer precipitate was collected by suction filtration and dried to obtain of poly(methyl methacrylate) (yield 100%).

GPC analysis [with reference to the molecular weight of an authentic sample of poly(methyl methacrylate)] revealed Mn=12,500 and PD=1.08.

Example 41

Along with 1.00 g (10 mmole) of methyl methacrylate (same as above), 26.7 mg (0.10 mmole) of ethyl 2-dimethylstibanyl-2-methylpropionate prepared in Example 1, 8.2 mg (0.05 mmol) of 2,2'-azobis(isobutyronitrile), 14.3 mg (0.05 mmol) of dimethyl ditelluride prepared in Preparation Example 3 and 9 mg of POVAL (same as above), and 3 g of distilled water fully deaerated by nitrogen bubbling. The mixture was irradiated with ultrasonic waves for 120 seconds to obtain a uniform dispersion. The dispersion was stirred at 60° C. for 20 hours. After the completion of the reaction, the reaction mixture was dissolved in 10 ml of chloroform, and the solution was placed into 300 ml of methanol with stirring. The resulting polymer precipitate was treated by suction filtration and dried, affording poly(methyl methacrylate) (94% in yield).

GPC analysis [with reference to the molecular weight of an authentic sample of poly(methyl methacrylate)] revealed Mn=10,200 and PD=1.28.

Example 42

Along with 1.00 g (10 mmole) of methyl methacrylate (same as above) and 22.0 mg (0.10 mmole) of 2-methyldimethylstibanyl-propionitrile prepared in Example 2 were placed into a glove box with the inside air replaced by nitrogen, followed by stirring at 10° C. for 24 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 99%).

GPC analysis [with reference to the molecular weight of an authentic sample of poly(methyl methacrylate)] revealed Mn=8,300 and PD=1.50.

Example 43

Along with 1.00 g (10 mmole) of methyl methacrylate (same as above), 22.0 mg (0.10 mmole) of 2-methyl-dimethylstibanyl-propionitrile prepared in Example 2 and 8.2 mg (0.05 mmol) of 2,2'-azobis(isobutyronitrile) were placed into a glove box with the inside air replaced by nitrogen, followed by stirring at 60° C. for 3.5 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 86%).

GPC analysis [with reference to the molecular weight of an authentic sample of poly(methyl methacrylate)] revealed Mn=12,100 and PD=1.37.

Example 44

Along with 1.00 g (10 mmole) of methyl methacrylate (same as above) and 25.7 mg (0.10 mmole) of (1-dimethylstibanyl-ethyl)benzene prepared in Example 3 were placed into a glove box with the inside air replaced by nitrogen, followed by stirring at 100° C. for 24 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 84%).

GPC analysis [with reference to the molecular weight of an authentic sample of poly(methyl methacrylate)] revealed Mn=9,400 and PD=1.21.

Example 45

Along with 1.00 g (10 mmole) of methyl methacrylate (same as above), 25.7 mg (0.10 mmole) of (1-dimethylstibanyl-ethyl)benzene prepared in Example 3 and 16.42 mg (0.10 mmol) of 2,2'-azobis(isobutyronitrile) were placed into a glove box with the inside air replaced by nitrogen, followed by stirring at 60° C. for 1.5 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(methyl methacrylate) (yield 95%).

GPC analysis [with reference to the molecular weight of an authentic sample of poly(methyl methacrylate)] revealed Mn=11,600 and PD=1.21.

Example 46

Along with 2.22 g (20.0 mmole) of 1-vinyl-2-pyrrolidone (same as above) and 106.8 mg (0.40 mmol) of ethyl 2-dimethylstibanyl-2-methylpropionate prepared in Example 1 were placed into a glove box with the inside air replaced by nitrogen, followed by stirring at 110° C. for 60 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain of poly(1-vinyl-2-pyrrolidone) (yield 63%).

GPC analysis [with reference to the molecular weight of an authentic sample of poly(methyl methacrylate)] revealed Mn=3,000 and PD=1.06.

Example 47

Along with 0.33 g (3.0 mmole) of 1-vinyl-2-pyrrolidone (same as above), 26.7 mg (0.10 mmol) of ethyl 2-dimethylstibanyl-2-methylpropionate prepared in Example 1 and 4.10 mg (0.025 mmol) of 2,2'-azobis(isobutyronitrile) were placed into a glove box with the inside air replaced by nitrogen, followed by stirring at 60° C. for 1 hour. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(1-vinyl-2-pyrrolidone) (yield 97%).

GPC analysis [with reference to the molecular weight of an authentic sample of poly(methyl methacrylate)] revealed Mn=3,100 and PD=1.07.

Example 48

Along with 1.39 g (12.5 mmole) of 1-vinyl-2-pyrrolidone (same as above), 26.7 mg (0.10 mmol) of ethyl 2-dimethylstibanyl-2-methylpropionate prepared in Example 1 and 8.21 mg (0.05 mmol) of 2,2'-azobis(isobutyronitrile) were placed into a glove box with the inside air replaced by nitrogen, followed by stirring at 60° C. for 1 hour. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(1-vinyl-2-pyrrolidone) (yield 96%).

GPC analysis [with reference to the molecular weight of an authentic sample of poly(methyl methacrylate)] revealed Mn=14,200 and PD=1.12.

Example 49

Along with 2.22 g (20.0 mmole) of 1-vinyl-2-pyrrolidone (same as above), 26.7 mg (0.10 mmol) of ethyl 2-dimethylstibanyl-2-methylpropionate prepared in Example 1 and 8.21 mg (0.05 mmol) of 2,2'-azobis(isobutyronitrile) were placed into a glove box with the inside air replaced by nitrogen, followed by stirring at 60° C. for 1 hour. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(1-vinyl-2-pyrrolidone) (yield 100%).

GPC analysis [with reference to the molecular weight of an authentic sample of poly(methyl methacrylate)] revealed Mn=28,300 and PD=1.09.

Example 50

Along with 7.77 g (70.0 mmole) of 1-vinyl-2-pyrrolidone (same as above), 26.7 mg (0.10 mmol) of ethyl 2-dimethylstibanyl-2-methylpropionate prepared in Example 1 and 8.21 mg (0.05 mmol) of 2,2'-azobis(isobutyronitrile) were placed into a glove box with the inside air replaced by nitrogen, followed by stirring at 60° C. for 2 hours. After the completion of the reaction, the reaction mixture was dissolved in 15 ml of chloroform, and the solution was then poured into 550 ml of hexane which was being stirred. The resulting polymer precipitate was collected by suction filtration and dried to obtain of poly(1-vinyl-2-pyrrolidone) (yield 99%).

GPC analysis [with reference to the molecular weight of an authentic sample of poly(methyl methacrylate)] revealed Mn=61,300 and PD=1.27.

Example 51

Along with 11.1 g (100.0 mmole) of 1-vinyl-2-pyrrolidone (same as above), 26.7 mg (0.10 mmol) of ethyl 2-dimethylstibanyl-2-methylpropionate prepared in Example 1 and 8.21 mg (0.05 mmol) of 2,2'-azobis(isobutyronitrile) were placed into a glove box with the inside air replaced by nitrogen, followed by stirring at 60° C. for 2 hours. After the completion of the reaction, the reaction mixture was dissolved in 20 ml of chloroform, and the solution was then poured into 750 ml of hexane which was being stirred. The resulting polymer precipitate was collected by suction filtration and dried to obtain of poly(1-vinyl-2-pyrrolidone) (yield 93%).

GPC analysis [with reference to the molecular weight of an authentic sample of poly(methyl methacrylate)] revealed Mn=83,500 and PD=1.29.

Example 52

Along with 2.0 g (18.0 mmole) of 1-vinyl-2-pyrrolidone (same as above), 17.8 mg (0.07 mmol) of ethyl 2-dimethylstibanyl-2-methylpropionate prepared in Example 1, 9.3 mg (0.03 mmol) of 4,4'-azobis(4-cyanovarelic acid) (Otsuka Chemical Co., Ltd., brand name: ACVA) and 2.0 g of distilled water were placed into a glove box with the inside air replaced by nitrogen, followed by stirring at 60° C. for 6 hours. After the completion of the reaction, the resulting polymer precipitate was collected by suction filtration and dried to obtain poly(1-vinyl-2-pyrrolidone) (yield 100%).

GPC analysis [with reference to the molecular weight of an authentic sample of poly(methyl methacrylate)] revealed Mn=25,900 and PD=1.12.

Example 53

Along with 1.11 g (10.0 mmole) of 1-vinyl-2-pyrrolidone (same as above), 22.0 mg (0.10 mmol) of 2-methyl 2-dimethylstibanyl-propionitrile prepared in Example 2 and 4.10 mg (0.025 mmol) of 2,2'-azobis(isobutyronitrile) were placed into a glove box with the inside air replaced by nitrogen, followed by stirring at 60° C. for 1.5 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(1-vinyl-2-pyrrolidone) (yield 94%).

GPC analysis [with reference to the molecular weight of an authentic sample of poly(methyl methacrylate)] revealed Mn=11,800 and PD=1.10.

Example 54

Along with 1.11 g (10.0 mmole) of 1-vinyl-2-pyrrolidone (same as above), 22.0 mg (0.10 mmol) of 2-methyl 2-dimethylstibanyl-propionitrile prepared in Example 2 and 8.21 mg (0.05 mmol) of 2,2'-azobis(isobutyronitrile) were placed into a glove box with the inside air replaced by nitrogen, followed by stirring at 60° C. for 0.8 hour. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(1-vinyl-2-pyrrolidone) (yield 95%).

GPC analysis [with reference to the molecular weight of an authentic sample of poly(methyl methacrylate)] revealed Mn=10,700 and PD=1.12.

Example 55

Along with 1.11 g (10.0 mmole) of 1-vinyl-2-pyrrolidone (same as above), 25.7 mg (0.10 mmol) of (1-dimethylstibanyl-ethyl)benzene prepared in Example 3 and 4.10 mg (0.025 mmol) of 2,2'-azobis(isobutyronitrile) were placed into a glove box with the inside air replaced by nitrogen, followed by stirring at 60° C. for 4 hours After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(1-vinyl-2-pyrrolidone) (yield 94%).

GPC analysis [with reference to the molecular weight of an authentic sample of poly(methyl methacrylate)] revealed Mn=11,100 and PD=1.12.

Example 56

Along with 1.11 g (10.0 mmole) of 1-vinyl-2-pyrrolidone (same as above), 25.7 mg (0.10 mmol) of (1-dimethylstibanyl-ethyl)benzene prepared in Example 3 and 8.21 mg (0.05 mmol) of 2,2'-azobis(isobutyronitrile) were placed into a glove box with the inside air replaced by nitrogen, followed by stirring at 60° C. for 0.5 hour. After the completion of the reaction, the reaction mixture was dissolved in 5 ml of chloroform, and the solution was then poured into 250 ml of hexane which was being stirred. The resulting polymer precipitate was collected by suction filtration and dried to obtain of poly(1-vinyl-2-pyrrolidone) (yield 100%).

GPC analysis [with reference to the molecular weight of an authentic sample of poly(methyl methacrylate)] revealed Mn=12,700 and PD=1.10.

Example 57

Along with 1.27 g (10.0 mmole) of N-isopropylmethacrylamide (Wako Pure Chemical Industries, Ltd.), 26.7 mg (0.10 mmol) of ethyl 2-dimethylstibanyl-2-methylpropionate prepared in Example 1, 16.4 mg (0.10 mmol) of 2,2'-azobis (isobutyronitrile) and 3 ml of N,N-dimethylformamide (DMF) were placed into a glove box with the inside air replaced by nitrogen, followed by stirring at 60° C. for 6 hours. After the completion of the reaction, the reaction mixture was dissolved in 3 ml of chloroform, and the solution was then poured into 200 ml of hexane which was being stirred. The resulting polymer precipitate was collected by suction filtration and dried to obtain poly(N-isopropylmethacrylamide) (yield 94%).

GPC analysis [with reference to the molecular weight of an authentic sample of poly(methyl methacrylate)] revealed Mn=24,100 and PD=1.39.

Example 58

Along with 0.99 g (10.0 mmole) of N,N-dimethylacrylamide (Wako Pure Chemical Industries, Ltd.), 26.7 mg (0.10 mmol) of ethyl 2-dimethylstibanyl-2-methylpropionate prepared in Example 1 and 4.1 mg (0.025 mmol) of 2,2'-azobis (isobutyronitrile) were placed into a glove box with the inside air replaced by nitrogen, followed by stirring at 60° C. for 20 hours. After the completion of the reaction, solvent and the remained monomer were removed under reduced pressure by vacuum pump to obtain poly(N,N-dimethylacrylamide) (yield 91%).

GPC analysis [with reference to the molecular weight of an authentic sample of poly(methyl methacrylate)] revealed Mn=10,100 and PD=1.22.

Example 59

Along with 0.99 g (10.0 mmole) of N,N-dimethylacrylamide (Wako Pure Chemical Industries, Ltd.), 26.7 mg (0.10 mmol) of ethyl 2-dimethylstibanyl-2-methylpropionate prepared in Example 1 and 8.21 mg (0.50 mmol) of 2,2'-azobis (isobutyronitrile) were placed into a glove box with the inside air replaced by nitrogen, followed by stirring at 60° C. for 20 hours. After the completion of the reaction, solvent and the remained monomer were removed under reduced pressure by vacuum pump to obtain poly(N,N-dimethylacrylamide) (yield 89%).

GPC analysis [with reference to the molecular weight of an authentic sample of poly(methyl methacrylate)] revealed Mn=8,400 and PD=1.29.

Example 60

Along with 0.99 g (10.0 mmole) of N,N-dimethylacrylamide (Wako Pure Chemical Industries, Ltd.), 22.0 mg (0.10 mmol) of 2-methyl-2-dimethylstibanyl-propionitrile prepared in Example 2 and 4.1 mg (0.025 mmol) of 2,2'-azobis (isobutyronitrile) were placed into a glove box with the inside air replaced by nitrogen, followed by stirring at 60° C. for 30 hours. After the completion of the reaction, solvent and the remained monomer were removed under reduced pressure by vacuum pump to obtain poly(N,N-dimethylacrylamide) (yield 96%).

GPC analysis [with reference to the molecular weight of an authentic sample of poly(methyl methacrylate)] revealed Mn=10,700 and PD=1.25.

Example 61

Along with 0.99 g (10.0 mmole) of N,N-dimethylacrylamide (Wako Pure Chemical Industries, Ltd.), 22.0 mg (0.10 mmol) of 2-methyl-2-dimethylstibanyl-propionitrile prepared in Example 2 and 8.21 mg (0.50 mmol) of 2,2'-azobis (isobutyronitrile) were placed into a glove box with the inside air replaced by nitrogen, followed by stirring at 60° C. for 20 hours. After the completion of the reaction, solvent and the remained monomer were removed under reduced pressure by vacuum pump to obtain poly(N,N-dimethylacrylamide) (yield 95%).

GPC analysis [with reference to the molecular weight of an authentic sample of poly(methyl methacrylate)] revealed Mn=8,700 and PD=1.27.

Example 62

Along with 0.99 g (10.0 mmole) of N,N-dimethylacrylamide (Wako Pure Chemical Industries, Ltd.), 25.7 mg (0.10 mmol) of (1-dimethylstibanyl-ethyl)benzene prepared in Example 3 and 4.1 mg (0.025 mmol) of 2,2'-azobis(isobutyronitrile) were placed into a glove box with the inside air replaced by nitrogen, followed by stirring at 60° C. for 30 hours. After the completion of the reaction, solvent and the remained monomer were removed under reduced pressure by vacuum pump to obtain poly(N,N-dimethylacrylamide) (yield 95%).

GPC analysis [with reference to the molecular weight of an authentic sample of poly(methyl methacrylate)] revealed Mn=11,400 and PD=1.20.

Example 63

Along with 0.99 g (10.0 mmole) of N,N-dimethylacrylamide (Wako Pure Chemical Industries, Ltd.), 25.7 mg (0.10 mmol) of (1-dimethylstibanyl-ethyl)benzene prepared in Example 3 and 8.21 mg (0.50 mmol) of 2,2'-azobis(isobutyronitrile) were placed into a glove box with the inside air replaced by nitrogen, followed by stirring at 60° C. for 20 hours. After the completion of the reaction, solvent and the remained monomer were removed under reduced pressure by vacuum pump to obtain poly(N,N-dimethylacrylamide) (yield 95%).

GPC analysis [with reference to the molecular weight of an authentic sample of poly(methyl methacrylate)] revealed Mn=10,200 and PD=1.24.

Example 64

Along with 2.08 g (20.0 mmole) of styrene (same as above) and 26.7 mg (0.10 mmol) of ethyl 2-dimethylstibanyl-2-methyl propionate prepared in Example 1 were placed into a glove box with the inside air replaced by nitrogen, followed by stirring at 110° C. for 24 hours. After the completion of the reaction, the reaction mixture was dissolved in 5 ml of chloroform, and the solution was then poured into 250 ml of methanol which was being stirred. The resulting polymer precipitate was collected by suction filtration and dried to obtain polystyrene macroinitiator.

GPC analysis [with reference to the molecular weight of an authentic sample of polystyrene] revealed Mn=24,200 and PD=1.11.

Example 65

Along with 0.25 g (2.2 mmole) of 1-vinyl-2-pyrrolidone, 0.20 mg (0.011 mmol) of polystyrene macroinitiator prepared in Example 64, 0.4 mg (0.003 mmol) of 2,2'-azobis(isobutyronitrile) and 1 ml of N,N-dimethylformamide (DMF) were placed into a glove box with the inside air replaced by nitrogen, followed by stirring at 60° C. for 24 hours. After the completion of the reaction, the reaction mixture was dissolved in 5 ml of chloroform, and the solution was then poured into 300 ml of diethyl ether which was being stirred. The resulting polymer precipitate was collected by suction filtration and dried to obtain block copolymer of poly(styrene-b-1-vinyl-2-pyrrolidone) (yield 77%).

GPC analysis [with reference to the molecular weight of an authentic sample of polystyrene] revealed Mn=50,900 and PD=1.27.

Example 66

Along with 0.99 g (8.9 mmole) of 1-vinyl-2-pyrrolidone, 0.33 g (0.018 mmol) of polystyrene macroinitiator prepared in Example 64, 0.7 mg (0.004 mmol) of 2,2'-azobis(isobutyronitrile) and 1.5 ml of N,N-dimethylformamide (DMF) were placed into a glove box with the inside air replaced by nitrogen, followed by stirring at 60° C. for 21 hours. After the completion of the reaction, the reaction mixture was dissolved in 5 ml of chloroform, and the solution was then poured into 300 ml of diethyl ether which was being stirred. The resulting polymer precipitate was collected by suction filtration and dried to obtain block copolymer of poly(styrene-b-1-vinyl-2-pyrrolidone) (yield 63%).

GPC analysis [with reference to the molecular weight of an authentic sample of polystyrene] revealed Mn=74,100 and PD=1.28.

Example 67

Along with 2.12 g (20 mmole) of 1-vinyl-2-pyrrolidone (same as above) and 106.8 g (0.40 mmol) of ethyl 2-dimethylstibanyl-2-methyl propionate prepared in Example 1 were placed into a glove box with the inside air replaced by nitrogen, followed by stirring at 100° C. for 60 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(1-vinyl-2-pyrrolidone) macroinitiator.

GPC analysis [with reference to the molecular weight of an authentic sample of poly(methyl methacrylate)] revealed Mn=2,800 and PD=1.06.

Example 68

Along with 0.20 g (0.07 mmol) of poly(1-vinyl-2-pyrrolidone) macroinitiator prepared in Example 67, 1 ml of N,N-dimethylformamide (DMF), 2.9 mg (0.018 mmol) of 2,2'-azobis(isobutyronitrile) and 0.74 g (7.1 mmole) of styrene were placed into a glove box with the inside air replaced by nitrogen, followed by stirring at 60° C. for 8 hours. After the completion of the reaction, the reaction mixture was dissolved in 5 ml of chloroform, and the solution was then poured into 300 ml of diethyl ether which was being stirred. The resulting polymer precipitate was collected by suction filtration and dried to obtain block copolymer of poly(1-vinyl-2-pyrrolidone-b-styrene) (yield 14%).

GPC analysis [with reference to the molecular weight of an authentic sample of polystyrene] revealed Mn=11,900 and PD=1.12.

Example 69

Along with 228 mg (0.08 mmol) of poly(1-vinyl-2-pyrrolidone) macroinitiator prepared in Example 67, 3.3 mg (0.02 mmol) of 2,2'-azobis(isobutyronitrile) and 1.04 g (8.1 mmole) of n-butyl acrylate (same as above) were placed into a glove box with the inside air replaced by nitrogen, followed by stirring at 60° C. for 6 hours. After the completion of the reaction, the reaction mixture was dissolved in 5 ml of N,N-dimethylformamide (DMF), and the solution was then poured into 300 ml of hexane which was being stirred. The resulting polymer precipitate was collected by suction filtration and dried to obtain block copolymer of poly(1-vinyl-2-pyrrolidone-b-n-butyl acrylate) (yield 94%).

GPC analysis [with reference to the molecular weight of an authentic sample of poly(methyl methacrylate)] revealed Mn=19,000 and PD=1.15.

Example 70

Along with 134 mg (0.046 mmol) of poly(1-vinyl-2-pyrrolidone) macroinitiator prepared in Example 67, 1.9 mg (0.011 mmol) of 2,2'-azobis(isobutyronitrile) and 0.244 g (4.6 mmole) of acrylonitrile (same as above) were placed into a glove box with the inside air replaced by nitrogen, followed by stirring at 60° C. for 8 hours. After the completion of the reaction, the reaction mixture was dissolved in 5 ml of N,N-dimethylformamide (DMF), and the solution was then poured into 300 ml of ether which was being stirred. The resulting polymer precipitate was collected by suction filtration and dried to obtain block copolymer of poly(1-vinyl-2-pyrrolidone-b-acrylonitrile) (yield 99%).

GPC analysis [with reference to the molecular weight of an authentic sample of poly(methyl methacrylate)] revealed Mn=34,600 and PD=1.07.

Example 71

Along with 2.33 g (22 mmole) of 1-vinyl-2-pyrrolidone (same as above) and 106.8 g (0.40 mmol) of ethyl 2-dimethylstibanyl-2-methyl propionate prepared in Example 1 were placed into a glove box with the inside air replaced by nitrogen, followed by stirring at 100° C. for 60 hours. After the completion of the reaction, the reaction mixture was dissolved in 5 ml of chloroform, and the solution was then poured into 250 ml of hexane which was being stirred. The resulting polymer precipitate was collected by suction filtration and dried to obtain poly(1-vinyl-2-pyrrolidone) macroinitiator.

GPC analysis [with reference to the molecular weight of an authentic sample of poly(methyl methacrylate)] revealed Mn=3,000 and PD=1.06.

Example 72

Along with 0.14 g (0.046 mmol) of poly(1-vinyl-2-pyrrolidone) macroinitiator prepared in Example 71, 1 ml of N,N-dimethylformamide (DMF), 1.9 mg (0.012 mmol) of 2,21-azobis(isobutyronitrile) and 0.46 g (4.6 mmole) of methyl methacrylate (same as above) were placed into a glove box with the inside air replaced by nitrogen, followed by stirring at 60° C. for 8 hours. After the completion of the reaction, the reaction mixture was dissolved in 5 ml of chloroform, and the solution was then poured into 300 ml of diethyl ether which was being stirred. The resulting polymer precipitate was collected by suction filtration and dried to obtain block copolymer of poly(1-vinyl-2-pyrrolidone-b-methyl methacrylate) (yield 88%).

GPC analysis [with reference to the molecular weight of an authentic sample of poly(methyl methacrylate)] revealed Mn=20,400 and PD=1.18.

Example 73

Along with 183 mg (0.065 mmol) of poly(1-vinyl-2-pyrrolidone) macroinitiator prepared in Example 71, 2.7 mg (0.016 mmol) of 2,2'-azobis(isobutyronitrile) and 0.734 g (6.4 mmole) of N-isopropylacrylamide (same as above) were placed into a glove box with the inside air replaced by nitrogen, followed by stirring at 60° C. for 6 hours. After the completion of the reaction, the reaction mixture was dissolved in 5 ml of N,N-dimethylformamide (DMF), and the solution was then poured into 300 ml of hexane which was being stirred. The resulting polymer precipitate was collected by suction filtration and dried to obtain block copolymer of poly(1-vinyl-2-pyrrolidone-b-N-isopropylacrylamide) (yield 99%).

GPC analysis [with reference to the molecular weight of an authentic sample of poly(methyl methacrylate)] revealed Mn=44,800 and PD=1.07.

Example 74

Along with 1.04 g (10 mmole) of styrene (same as above) and 66.8 mg (0.25 mmol) of ethyl 2-dimethylstibanyl-2-methyl propionate prepared in Example 1 were placed into a glove box with the inside air replaced by nitrogen, followed by stirring at 110° C. for 24 hours. After the completion of the reaction, the reaction mixture was dissolved in 5 ml of chloroform, and the solution was then poured into 250 ml of methanol which was being stirred. The resulting polymer precipitate was collected by suction filtration and dried to obtain polystyrene macroinitiator.

GPC analysis [with reference to the molecular weight of an authentic sample of polystyrene] revealed Mn=4,100 and PD=1.04.

Example 75

Along with 188 mg (0.046 mmol) of polystyrene macroinitiator prepared in Example 74, 1.9 mg (0.011 mmol) of 2,2'-azobis(isobutyronitrile), 0.46 g (4.6 mmole) of methyl methacrylate (same as above) and 1 ml of N,N-dimethylformamide (DMF) were placed into a glove box with the inside air replaced by nitrogen, followed by stirring at 60° C. for 9 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain block copolymer of poly(styrene-b-methyl methacrylate) (yield 89%).

GPC analysis [with reference to the molecular weight of an authentic sample of polystyrene] revealed Mn=11,000 and PD=1.17.

Example 76

Along with 204 mg (0.050 mmol) of polystyrene macroinitiator prepared in Example 74, 2.0 mg (0.012 mmol) of 2,2'-azobis(isobutyronitrile), 0.26 g (5.0 mmole) of acrylonitrile (same as above) and 1 ml of N,N-dimethylformamide (DMF) were placed into a glove box with the inside air replaced by nitrogen, followed by stirring at 60° C. for 6 hours. After the completion of the reaction, the reaction mixture was dissolved in 5 ml of chloroform, and the solution was then poured into 300 ml of methanol which was being stirred. The resulting polymer precipitate was collected by suction filtration and dried to obtain block copolymer of poly(styrene-b-acrylonitrile) (yield 82%).

GPC analysis [with reference to the molecular weight of an authentic sample of polystyrene] revealed Mn=27,800 and PD=1.20.

Example 77

Along with 0.54 g (5 mmole) of styrene (same as above) and 26.7 mg (0.10 mmol) of ethyl 2-dimethylstibanyl-2-methylpropionate prepared in Example 1 were placed into a glove box with the inside air replaced by nitrogen, followed by stirring at 110° C. for 24 hours. After the completion of the reaction, the reaction mixture was dissolved in 5 ml of chloroform, and the solution was then poured into 250 ml of methanol which was being stirred. The resulting polymer precipitate was collected by suction filtration and dried to obtain polystyrene macroinitiator.

GPC analysis [with reference to the molecular weight of an authentic sample of polystyrene] revealed Mn=5,400 and PD=1.07.

Example 78

Along with 264 mg (0.049 mmol) of polystyrene macroinitiator prepared in Example 77, 0.9 mg (0.005 mmol) of 2,2'-azobis(isobutyronitrile), 0.62 g (4.9 mmole) of n-butyl acrylate (same as above) and 1 ml of N,N-dimethylformamide (DMF) were placed into a glove box with the inside air replaced by nitrogen, followed by stirring at 60° C. for 4 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain block copolymer of poly(styrene-b-n-butyl acrylate) (yield 94%).

GPC analysis [with reference to the molecular weight of an authentic sample of polystyrene] revealed Mn=13,300 and PD=1.23.

Example 79

Along with 249 mg (0.046 mmol) of polystyrene macroinitiator prepared in Example 77, 1.8 mg (0.011 mmol) of 2,2'-azobis(isobutyronitrile), 0.52 g (4.6 mmole) of N-isopropylacrylamide (same as above) and 1 ml of N,N-dimethylformamide (DMF) were placed into a glove box with the inside air replaced by nitrogen, followed by stirring at 60° C. for 6 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain block copolymer of poly(styrene-b-N-isopropylacrylamide) (yield 99%).

GPC analysis [with reference to the molecular weight of an authentic sample of polystyrene] revealed Mn=34,500 and PD=1.05.

Example 80

Along with 0.5 g (5 mmole) of methyl methacrylate (same as above) and 26.7 mg (0.10 mmol) of ethyl 2-dimethylstibanyl-2-methyl propionate prepared in Example 1 were placed into a glove box with the inside air replaced by nitrogen, followed by stirring at 110° C. for 24 hours. After the completion of the reaction, the reaction mixture was dissolved in 5 ml of chloroform, and the solution was then poured into 250 ml of methanol which was being stirred. The resulting polymer precipitate was collected by suction filtration and dried to obtain poly(methyl methacrylate) macroinitiator.

GPC analysis [with reference to the molecular weight of an authentic sample of poly(methyl methacrylate)] revealed Mn=4,700 and PD=1.27.

Example 81

Along with 230 mg (0.055 mmole) of poly(methyl methacrylate) macroinitiator prepared in Example 80, 0.9 mg (0.005 mmol) of 2,2'-azobis(isobutyronitrile), 0.70 g (5.5 mmole) of n-butyl acrylate (same as above) and 1 ml of N,N-dimethylformamide (DMF) were placed into a glove box with the inside air replaced by nitrogen, followed by stirring at 60° C. for 3 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain block copolymer of poly(methyl methacrylate-b-n-butyl acrylate) (yield 97%).

GPC analysis [with reference to the molecular weight of an authentic sample of poly(methyl methacrylate)] revealed Mn=20,600 and PD=1.25.

Example 82

Along with 66 mg (0.016 mmole) of poly(methyl methacrylate) macroinitiator prepared in Example 80, 0.6 mg (0.004 mmol) of 2,2'-azobis(isobutyronitrile), 0.18 g (1.6 mmole) of N-isopropylacrylamide (same as above) and 1 ml of N,N-dimethylformamide (DMF) were placed into a glove box with the inside air replaced by nitrogen, followed by stirring at 60° C. for 3 hours. After the completion of the reaction, the reaction mixture was dissolved in 5 ml of chloroform, and the solution was then poured into 300 ml of hexane which was being stirred. The resulting polymer precipitate was collected by suction filtration and dried to obtain block copolymer of poly(methyl methacrylate-b-N-isopropylacrylamide) (yield 96%).

GPC analysis [with reference to the molecular weight of an authentic sample of poly(methyl methacrylate)] revealed Mn=21,600 and PD=1.15.

Example 83

Along with 146 mg (0.035 mmol) of poly(methyl methacrylate) macroinitiator prepared in Example 80, 1.4 mg (0.009 mmol) of 2,2'-azobis(isobutyronitrile), 0.18 g (3.5 mmole) of acrylonitrile (same as above) and 1 ml of N,N-dimethylformamide (DMF) were placed into a glove box with the inside air replaced by nitrogen, followed by stirring at 60° C. for 8 hours. After the completion of the reaction, the reaction mixture was dissolved in 5 ml of chloroform, and the solution was then poured into 300 ml of methanol which was being stirred. The resulting polymer precipitate was collected by suction filtration and dried to obtain block copolymer of poly(methyl methacrylate-b-acrylonitrile) (yield 62%).

GPC analysis [with reference to the molecular weight of an authentic sample of poly(methyl methacrylate)] revealed Mn=25,400 and PD=1.31.

Example 84

Along with 0.64 g (6 mmole) of N-isopropyl methacrylamide (same as above), 0.57 g (5 mmole) of N-isopropylacrylamide (same as above), 26.7 mg (0.10 mmol) of ethyl 2-dimethylstibanyl-2-methylpropionate prepared in Example 1, 16.4 mg (0.10 mmol) of 2,2'-azobis(isobutyronitrile) and 3 ml of N,N-dimethylformamide (DMF) were placed into a glove box with the inside air replaced by nitrogen, followed by stirring at 60° C. for 18 hours. After the completion of the reaction, the reaction mixture was dissolved in 3 ml of chloroform, and the solution was then poured into 200 ml of hexane which was being stirred. The resulting polymer precipitate was collected by suction filtration and dried to obtain poly(N-isopropylmethacryl amide-r-N-isopropylacrylamide) (yield 95%).

GPC analysis [with reference to the molecular weight of an authentic sample of poly(methyl methacrylate)] revealed Mn=24,100 and PD=1.39.

Example 85

Stirred in a glove box having its inside air replaced by nitrogen at 60° C. for 6 hours were 0.8 g (3.41 mmole) of an adamantane monomer MADM, 1.2 g (5.40 mmole) a norbornene monomer NBLM, 53.4 mg (0.20 mmole) of the ethyl 2-dimethylstibanyl-2-methylpropionate prepared in Example 1, 8.2 mg (0.05 mmole) of 2,2'-azobis(isobutyronitrile) and 2 g of toluene (the same as above). After the completion of the reaction, a solution of 436.5 mg (1.5 mmole) of tributyltin hydride (product of Aldrich) and 24.8 mg (0.15 mmole) of AIBN in 2 ml of toluene was added to the reaction mixture, followed by stirring at 60° C. for 2 hours. After the completion of the reaction, the reaction mixture was diluted with 2 ml of THF and then placed into 300 ml of methanol with stirring. The resulting polymer precipitate was treated by suction filtration, the polymer obtained was dissolved in 10 ml of 2-butanone again, and the solution was passed through a column made of activated alumina (product of Wako Pure Chemical Ind. Ltd.). The solution was thereafter poured into 100 ml of methanol. The resulting polymer precipitate was treated by suction filtration at room temperature and dried, giving poly(MADM-r-NBLM) (1.9 g, 95% in yield).

GPC analysis (with reference to the molecular weight of authentic sample of polymethyl methacrylate) revealed that the resin was 7,700 in Mn and 1.38 in PD. The resin was soluble in propylene glycol monomethyl ether acetate.

Example 86

Stirred in a glove box having its inside air replaced by nitrogen at 60° C. for 6 hours were 0.8 g (3.41 mmole) of an adamantane monomer MADM, 1.2 g (5.40 mmole) a norbornene monomer NBLM, 53.4 mg (0.20 mmole) of the ethyl 2-dimethylstibanyl-2-methylpropionate prepared in Example 1, 8.2 mg (0.05 mmole) of 2,2'-azobis(isobutyronitrile), 57.1 mg (0.20 mmole) of the dimethyl ditelluride prepared in Preparation Example 3 and 2 g of 2-butanone. After the completion of the reaction, a solution of 523.8 mg (1.8 mmole) of tributyltin hydride (the same as above) and 29.8 mg (0.18 mmole) of AIBN in 2 ml of 2-butanone was added to the reaction mixture, followed by stirring at 60° C. for 2 hours. After the completion of the reaction, the reaction mixture was diluted with 2 ml of 2-butanone and then placed into 300 ml of methanol with stirring. The resulting polymer precipitate was treated by suction filtration at room temperature, the polymer obtained was dissolved in 10 ml of 2-butanone again, and the solution was passed through a column made of activated alumina (the same as above). The solution was thereafter poured into 100 ml of methanol. The resulting polymer precipitate was treated by suction filtration at room temperature and dried, giving poly(MADM-r-NBLM) (1.84 g, 92% in yield).

GPC analysis (with reference to the molecular weight of authentic sample of polymethyl methacrylate) revealed that the resin was 8,800 in Mn and 1.21 in PD. The resin was soluble in propylene glycol monomethyl ether acetate.

INDUSTRIAL APPLICABILITY

The invention provides an organoantimony compound useful as a living radical polymerization initiator which realizes precision control of molecular weights and molecular weight distributions (PD=Mw/Mn) under mild conditions, processes for preparing the compound, processes for preparing polymers using the compound, and the polymers. The living radical polymers obtained by the polymerization process of the invention readily permit conversion of terminal groups to other functional groups, are useful for preparing macromonomers and useful as crosslinking sites and are usable as compatibilizing agents and as materials for block polymers.

A resin containing an acid-dissociable group is highly soluble in resist solvents and can be used suitably for resists for use in manufacturing semiconductor devices which are expected to be finer in structure.

The invention claimed is:

1. An organoantimony compound represented by the formula (1):

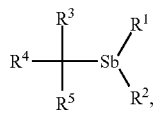

wherein $R^1$ and $R^2$ are $C_1$-$C_8$ alkyl, aryl, substituted aryl, or an aromatic heterocyclic group; $R^3$ and $R^4$ are each a hydrogen atom or $C_1$-$C_8$ alkyl; and $R^5$ is an aryl group unsubstituted or substituted by halogen, hydroxyl, alkoxyl, amino, nitro, cyano, —$COR^a$ (wherein $R^a$ is $C_1$-$C_8$ alkyl, aryl, $C_1$-$C_8$ alkoxyl, or aryloxyl), sulfonyl, or trifluoromethyl, an aromatic heterocyclic group, oxycarbonyl, or cyano;

provided that $R^3$ and $R^4$ are not hydrogen atoms simultaneously.

2. A process for preparing an organoantimony compound of the formula (1) of claim 1 comprising reacting a compound of the formula (3):

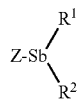

(wherein $R^1$ and $R^2$ are as defined previously, and Z is a halogen atom or an alkali metal)

and a compound of the formula (4) or (5):

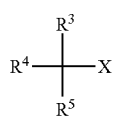

(wherein $R^3$, $R^4$, and $R^5$ are as defined previously, and X is a halogen atom)

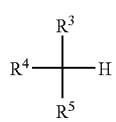

(wherein $R^3$, $R^4$, and $R^5$ are as defined previously).

3. A living radical polymerization initiator represented by the formula (2):

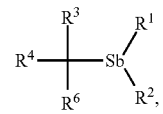

wherein $R^1$ and $R^2$ are $C_1$-$C_8$ alkyl, aryl, substituted aryl, or an aromatic heterocyclic group; $R^3$ and $R^4$ are each a hydrogen atom or $C_1$-$C_8$ alkyl; and $R^6$ is an aryl group unsubstituted or substituted by halogen, hydroxyl, alkoxyl, amino, nitro, cyano, —$COR^a$ (wherein $R^a$ is $C_1$-$C_8$ alkyl, aryl, $C_1$-$C_8$ alkoxyl, or aryloxyl), sulfonyl, or trifluoromethyl, an aromatic heterocyclic group, oxycarbonyl, or cyano.

4. A process for producing a living radical polymer wherein a vinyl monomer is polymerized with use of a living radical polymerization initiator of the formula (2) of claim 3.

5. A process for producing a living radical polymer wherein a vinyl monomer is polymerized with use of a living radical polymerization initiator of the formula (2) of claim 3 and an azo type polymerization initiator.

6. A mixture of a living radical polymerization initiator of the formula (2) of claim 3 and an azo type polymerization initiator.

7. A process for producing a random copolymer wherein at least two vinyl monomers are polymerized with use of a living radical polymerization initiator of the formula (2) of claim 3.

8. A process for producing a random copolymer wherein at least two vinyl monomers are polymerized with use of a living radical polymerization initiator of the formula (2) of claim 3 and an azo type polymerization initiator.

9. A macro living radical polymerization initiator which is obtainable by subjecting a vinyl monomer to polymerization with use of a living radical polymerization initiator of the formula (2) of claim 3.

10. A macro living radical polymerization initiator which is obtainable by subjecting a vinyl monomer to polymerization with use of a living radical polymerization initiator of the formula (2) of claim 3 and an azo type polymerization initiator.

11. A process for producing a block copolymer wherein a vinyl monomer is polymerized with use of a macro living radical polymerization initiator of claim 9.

12. A process for producing a block copolymer wherein a vinyl monomer is polymerized with use of a macro living radical polymerization initiator of claim 10.

13. A process for producing a living radical polymer wherein a vinyl monomer is polymerized with use of a mixture of a living radical polymerization initiator of the formula (2) of claim 3, and at least one compound selected from a ditelluride compound, a distibine compound, and a dibismuthine compound.

14. A process for producing a living radical polymer wherein a vinyl monomer is polymerized with use of a mixture of a living radical polymerization initiator of the formula (2) of claim 3, an azo type polymerization initiator, and at least one compound selected from a ditelluride compound, a distibine compound, and a dibismuthine compound.

15. A living radical polymer which is obtainable by subjecting a vinyl monomer to polymerization with use of a mixture of a living radical polymerization initiator of the formula (2) of claim 3, and at least one compound selected from a ditelluride compound, a distibine compound, and a dibismuthine compound.

16. A living radical polymer which is obtainable by subjecting a vinyl monomer to polymerization with use of a mixture of a living radical polymerization initiator of the formula (2) of claim 3, an azo type polymerization initiator, and at least one compound selected from a ditelluride compound, a distibine compound, and a dibismuthine compound.

17. A mixture of a living radical polymerization initiator of the formula (2) of claim 3, and at least one compound selected from a ditelluride compound, a distibine compound, and a dibismuthine compound.

18. A mixture of a living radical polymerization initiator of the formula (2) of claim 3, an azo type polymerization initiator, and at least one compound selected from a ditelluride compound, a distibine compound, and a dibismuthine compound.

19. A process for producing a random copolymer wherein at least two vinyl monomers are polymerized with use of a mixture of a living radical polymerization initiator of the formula (2) of claim 3, and at least one compound selected from a ditelluride compound, a distibine compound, and a dibismuthine compound.

20. A process for producing a random copolymer wherein at least two vinyl monomers are polymerized with use of a mixture of a living radical polymerization initiator of the formula (2) of claim 3, an azo type polymerization initiator, and at least one compound selected from a ditelluride compound, a distibine compound, and a dibismuthine compound.

21. A macro living radical polymerization initiator which is obtainable by subjecting a vinyl monomer to polymerization with use of a mixture of a living radical polymerization initiator of the formula (2) of claim 3, and at least one compound selected from a ditelluride compound, a distibine compound, and a dibismuthine compound.

22. A macro living radical polymerization initiator which is obtainable by subjecting a vinyl monomer to polymerization with use of a mixture of a living radical polymerization initiator of the formula (2) of claim 3, an azo type polymerization initiator, and at least one compound selected from ditelluride compound, a distibine compound, and a dibismuthine compound.

23. A process for producing a block copolymer wherein a vinyl monomer is polymerized with use of the macro living radical polymerization initiator of claim 21.

24. A process for producing a block copolymer wherein a vinyl monomer is polymerized with use of the macro living radical polymerization initiator of claim 22.

25. A process for producing a resin containing an acid-dissociable group wherein a vinyl monomer is polymerized with use of one of the following (a) to (d):
 (a) a living radical polymerization initiator of the formula (2) of claim 3;
 (b) a mixture of a living radical polymerization initiator of the formula (2), and an azo type polymerization initiator;
 (c) a mixture of a living radical polymerization initiator of the formula (2), and at least one compound selected from a ditelluride compound, a distibine compound, and a dibismuthine compound; and
 (d) a mixture of a living radical polymerization initiator of the formula (2), an azo type polymerization initiator, and at least one compound selected from a ditelluride compound, a distibine compound, and a dibismuthine compound.

* * * * *